(12) United States Patent  
Vergona

(10) Patent No.: US 7,178,571 B2  
(45) Date of Patent: Feb. 20, 2007

(54) SYSTEM AND METHOD FOR INCORPORATING GRAPHICS INTO ABSORBENT ARTICLES

(75) Inventor: Joseph B. Vergona, Suwanee, GA (US)

(73) Assignee: Tyco Healthcare Retail Services AG, Schaffhausen (CH)

( * ) Notice: Subject to any disclaimer, the term of this patent is extended or adjusted under 35 U.S.C. 154(b) by 0 days.

(21) Appl. No.: 10/979,173

(22) Filed: Nov. 3, 2004

(65) Prior Publication Data

US 2005/0092427 A1 May 5, 2005

Related U.S. Application Data

(62) Division of application No. 10/673,344, filed on Sep. 30, 2003.

(51) Int. Cl.  
*B32B 37/20* (2006.01)

(52) U.S. Cl. .................. 156/353; 156/361; 156/378; 101/481; 101/486; 101/485; 83/362

(58) Field of Classification Search .............. 156/64, 156/353, 361, 378, 384, 543, 550; 101/481, 101/484, 485, 486; 83/76, 361, 362, 363, 83/399, 400  
See application file for complete search history.

(56) References Cited

U.S. PATENT DOCUMENTS

| | | | |
|---|---|---|---|
| 5,003,876 A | 4/1991 | Harrison et al. | |
| 5,597,642 A | 1/1997 | Schleinz et al. | |
| 5,659,538 A | 8/1997 | Stuebe et al. | |
| 5,897,541 A | 4/1999 | Uitenbroek et al. | |
| 6,075,178 A | 6/2000 | La Wilhelm et al. | |
| 6,101,912 A * | 8/2000 | Sanders et al. | 83/53 |
| 6,888,083 B2 * | 5/2005 | Hergeth | 209/576 |

* cited by examiner

*Primary Examiner*—George Koch  
(74) *Attorney, Agent, or Firm*—Goszj & Partners LLP

(57) ABSTRACT

A method for incorporating graphics into absorbent articles. The method involving: providing a moving substrate to a print cylinder; sensing a line speed reference signal from a line speed target machinery component; rotating the print cylinder at a predetermined speed, based on the line speed reference signal, to thereby print a series of graphics on the moving substrate at a predetermined distance frequency; sensing a phase difference signal from a phase target machinery component; and setting an actual print cylinder phase angle, based on the phase difference signal, to approximate a predetermined phase angle to thereby position the series of graphics on the moving substrate at a series of desired graphics locations. A system for executing the method and garments produced from the method and system are also provided.

28 Claims, 8 Drawing Sheets

SYSTEM AND METHOD FOR INCORPORATING GRAPHICS INTO ABSORBENT ARTICLES

This application is a divisional of U.S. patent application Ser. No. 10/673,344 filed Sep. 30, 2003, the contents of which are incorporated herein by reference in their entirety.

FIELD OF THE INVENTION

The present invention relates to disposable absorbent articles, and more particularly to disposable absorbent articles having graphics thereon, and processes for making the same.

BACKGROUND OF THE INVENTION

Traditionally, disposable absorbent articles, such as infant diapers or training pants, adult incontinence products and other such products, are constructed with a moisture-impervious outer backing sheet (or "backsheet"), a moisture-pervious body-contacting inner liner sheet (or "topsheet"), and a moisture-absorbent core (or "absorbent core") sandwiched between the liner sheet and the backing sheets. These disposable absorbent articles oftentimes include additional features such as elastic waist bands, elastic leg bands, and stretchable side panels. Further, decorative graphics can be incorporated into the disposable absorbent article for aesthetic and functional purposes.

Disposable absorbent articles are generally assembled on an automated production line by separately supplying the individual components of the absorbent article to the production line at predetermined locations along the machine direction, and layering the individual components to form an integrated absorbent article. Various methods are available for bringing these individual components together so that the components in the integrated product are in a desired relation with respect to each other. In bringing these individual components together, various known methods have been used to sense the position of a particular component, and then to adjust the placement of subsequent components in order to properly position them with respect to the previously sensed component.

Prior art methods for assembling components of absorbent articles have employed photo/optical techniques to sense reference markers on the individual components. The reference markers assist in cutting and placing the individual components onto the integrated absorbent article. The reference markers have typically been included in the final assembled product. This is so because the reference markers employed in prior techniques need to be sensed downstream in the production line to provide error correction, requiring complex feed-back control systems. However, the inclusion of the reference markers on the final assembled product can detract from the aesthetics of the product and are therefore not desirable. These methods have, in particular, been used to incorporate decorative graphics into absorbent garments.

For example, U.S. Pat. No. 5,286,543 ("the '543 patent"), U.S. Pat. Nos. 5,235,515 and 5,286,543 to Ungpiyakul et al. disclose a system for selectively providing predetermined segments of web material to an absorbent article production line using a reference marker that is incorporated into the final assembled absorbent article. The predetermined segments of web material comprise discrete graphic patches corresponding to the tape landing zone of the diaper that are provided on a continuous, pre-printed roll. Each patch is said to have a predetermined set of graphics that are "congruously entire." The patches are also said to abruptly change from graphics set to graphics set and, therefore, from diaper to diaper because there is no modulating transition between the adjacent compositions formed on the original supply roll of web material. The patches are said to be provided with reference markers delineating the boundaries between individual web or patch segments. The reference markers comprise any signaling mechanism that is recognizable by a machine.

During the production of the absorbent article according to the '543 patent, a first sensing means detects the reference marker associated with the graphic as the web containing the graphics is unwound. Then, at a remote position in the manufacturing process, a second sensor observes the portions of the reference markers that remain permanently attached to each web segment. If the web segment is not correctly cut, the remote, second sensor detects this improper separation of the graphic and corrects for any improper cutting of the web segment by generating an updated set reference value based on where the remote, second sensor observes the reference marker downstream in the manufacturing line. The system is then selectively adjusted to incorporate the updated set reference value to assure that subsequent patches of web material are properly cut and positioned with respect to the other components forming the absorbent article.

The '543 patent at col. 14, lines 24–55 admits to be distinguishable from so-called "conventional techniques" employing, for example, a "shift register" scheme, for matching detector information to a particular manufacturing operation, such as the operation of a cutter. The so-called conventional techniques are said not to be capable of withstanding severe process disturbances. These disturbances, described as start-ups, splices within various web materials, and non-uniform stretching of web material caused by a non-uniform winding of the web materials onto the associated supply roll, are said to cause an improper placement of a significant number of patches and thereby increase cost and waste.

To overcome process disturbances, the so-called conventional techniques discussed in the '543 patent are said to be sensitive to the distance between the sensing means for detecting the reference marker and the cutting mechanism. In other words, the reference marker sensor in the conventional techniques had to be placed relatively close to the cutting mechanism because, if for example, a detector is mounted a relatively large distance, such as 25 web segment lengths before the cutting unit, the phasing mechanism can phase 25 patches too soon. Where a new roll of material is spliced onto an expiring roll with the sets of patch graphics on the new roll being "out of phase" from the previous roll, up to 25 patches may be cut incorrectly. Furthermore, the '543 patent states that in conventional techniques in which the detector is mounted a large distance from the cutter, the individual sets of print design graphics may not be exactly equally spaced, and the relative position of the patch graphics measured at the detector may not accurately represent the relative position of the patch graphics when the web material reaches the cutting mechanism. Due to this, the '543 patent recognizes that the greater the distance between the detector and the cutting mechanism, the larger the errors can be.

To eliminate these processing errors in the situation where the sensor and the cutting mechanism are remote from one another, the '543 patent employs feedback control in a manner where the reference marker (i) is not removed following its initial sensing by the first sensor, and (ii) is applied to the final assembled absorbent article for subsequent reading by the second, remote sensor. Consequently, the reference marker in the '543 patent, by virtue of being on the final absorbent article, is constructed to provide for a selected separating of discrete graphics. Indeed, without the reference marker on the final absorbent article in the '543 patent, feedback control is effectively eliminated from the system described in the '543 patent, and concomitantly process disturbances evidently will be permitted to cause the improper cutting and/or placement of the graphic, leading to a graphic that is neither aesthetically pleasing nor congruously entire.

Thus, the reference marker portions that remain upon each patch of web material in the final article of the '543 patent are "constructed to provide for a selected separating" of the graphic sets by enabling both the upstream first sensor and the downstream second sensor to detect the location of the reference marker portion and thereby register and control the location and cutting of the predetermined graphic sets. A claimed aspect of the invention of the '543 patent is the use of the reference marker portions to provide for the "selected separating" of the graphic sets. This "selected separating" employs an automated registration and "set point error" correction control loop using feedback from the second sensor. The second sensor detects the reference marker portions located on the patches of web material to enable the feedback control and thereby "provide for a selected separating" of the graphic sets.

But even though the so-called conventional techniques described in the '543 patent do not employ the reference marker later in the process line, they still apparently leave the reference marker on the final, assembled absorbent article. As noted previously, the reference markers in some instances are aesthetically displeasing, so leaving them on the final assembled absorbent article can detract from the presentation of the article.

Similarly, U.S. Pat. No. 5,766,389 to Brandon et al. discloses a process for controllably registering a plurality of components of a continuously moving first layer with a plurality of reference marks on a continuously moving second layer with pre-printed graphics. Brandon's registration process comprises the steps of (1) providing a continuously moving first layer having a plurality of components thereon, (2) providing a continuously moving second layer having a plurality of reference marks thereon, (3) sensing the distance between two successive reference marks, (4) generating a signal in response to the sensed distance, (5) adjusting the distance between subsequent successive reference marks to a selected distance, (6) joining the continuously moving first and second layers together, (7) sensing the position of each reference mark relative to its associated component, (8) generating a signal when one of the reference marks is out of position relative to its component, (9) processing the signal in accordance with preprogrammed instructions to generate a speed command signal, and (10) adjusting the speed of the continuously moving second layer in response to the speed command signal in accordance with preprogrammed instructions.

According to these prior methods, the assembled absorbent article must contain the sensed reference marker(s) to properly enable the complex feed-back control systems of the registration process. The inclusion of the reference marker(s) in the assembled product can detract from the aesthetic qualities of the final absorbent article, and the feed-back control can overly complicate the production line. For example, Procter & Gamble's Pampers™ Baby-Dry™ (tape closure system) and Pampers™ Rash Guard™ (hook and loop closure system) diapers include a reference marker on the closure landing systems, which apparently assists in cutting and placing the graphic on the assembled absorbent article. This marker is visibly apparent in the final assembled product, and detracts from the graphic on the tape landing zone. Further, the assembly and layering of the component parts in the machine direction, as shown in the prior art, limits the flexibility of the production line to incorporate a variety of different graphics into the integrated absorbent article.

In addition to the shortcomings described above, the prior art attempts at placing decorative graphics on absorbent garments are both expensive and, because of their complexity, sensitive to equipment and programming failures. These and other disadvantageous features of the prior art are overcome by the invention according to the preferred embodiments.

SUMMARY OF THE INVENTION

In response to the discussed difficulties and problems encountered in the prior art, a system and method for manufacturing absorbent articles with incorporated graphics, and articles manufactured by the method, have been discovered.

In a first embodiment, the present invention provides a method for incorporating graphics into absorbent articles. The method has the steps of: providing a moving substrate to a print cylinder; sensing a line speed reference signal from a line speed target machinery component; rotating the print cylinder at a predetermined speed, based on the line speed reference signal, to thereby print a series of graphics on the moving substrate at a predetermined distance frequency; sensing a phase difference signal from a phase target machinery component; and setting an actual print cylinder phase angle, based on the phase difference signal, to approximate a predetermined phase angle to thereby position the series of graphics on the moving substrate at a series of desired graphics locations.

In one embodiment of the invention, the substrate is a backsheet web. In this embodiment, the method may further include the steps of: providing a supply of absorbent pads; providing a topsheet web; joining the topsheet web to the backsheet web with the absorbent pads located therebetween to thereby form an absorbent core assembly; and cutting the absorbent core assembly at a series of cuts with a cutter. In this embodiment, the phase target machinery component is the cutter.

In various embodiment, the line speed target machinery component may be a main drive or a cutter. Also, ion one embodiment, the phase target machinery component may be a cutter. Still further, the line speed target machinery component and the phase target machinery component may be different machinery components or the same machinery component.

In various other embodiments, the line speed reference signal may be generated by an encoder, and the phase difference signal may be generated by an inductance sensor. In further embodiments, the series of graphics may be a series of wetness indicators or a series of combined wetness indicators and decorative graphics. In another embodiment, the print cylinder may be a flexographic print cylinder.

In still another embodiment, the invention may further comprise the steps of: providing the moving substrate to a second print cylinder; and rotating the second print cylinder at the predetermined speed, to thereby print a second series of graphics on the moving substrate at the predetermined distance frequency. In this embodiment, the series of graphics may be a series of wetness indicators and the second series of graphics may be a series of decorative graphics.

In yet another embodiment, the invention may comprise the steps of: detecting a shutdown mode from the line speed reference signal; disengaging the print cylinder from the substrate; and rotating the print cylinder at an idle speed. In another embodiment, the invention may comprise: detecting a startup mode from the line speed reference signal; accelerating the print cylinder from an idle speed to the predetermined speed; and engaging the print cylinder with the moving substrate.

In another embodiment, the present invention provides a system adapted to perform the method of the invention. In yet another embodiment, an absorbent article may be manufactured using the inventive system or method. The absorbent article may be a baby diaper, a baby training pant, or an adult incontinence article.

In still other embodiments, the print cylinder may be replaced by a graphic applicator, and in one such embodiment the graphic applicator is a cut-and-place device.

These and other objects, features and advantages of the preferred embodiments will become more readily apparent upon reading of the detailed description of the preferred embodiments of this invention in conjunction with the following drawings.

DETAILED DESCRIPTION OF THE PREFERRED EMBODIMENTS

Figure 1:
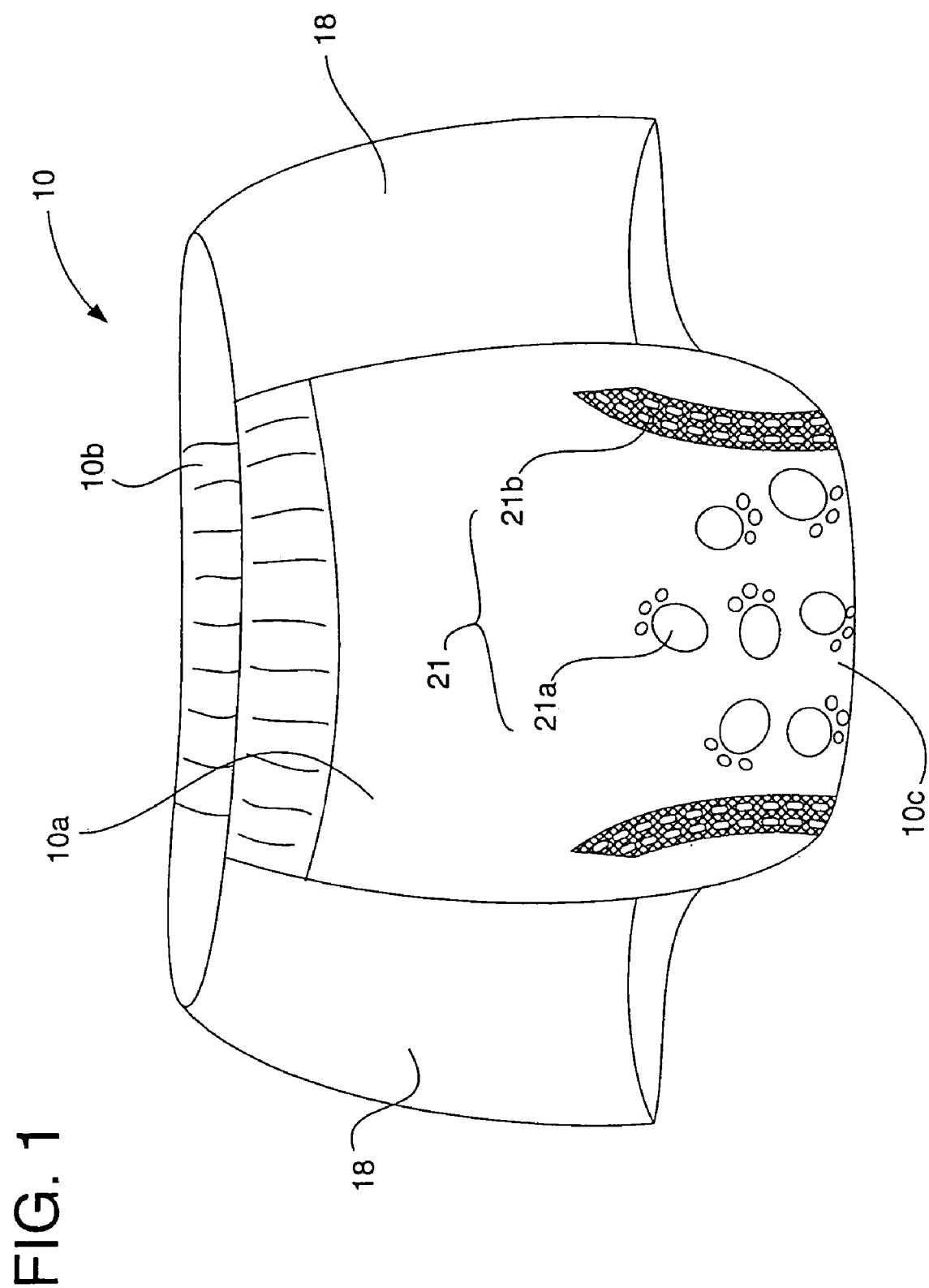
FIG. 1 illustrates a child's training pant with a graphic thereon according to the preferred embodiments.

As used herein, the terms "absorbent garment," "garment," "absorbent article" and "article" refer to garments that absorb and contain exudates, and more specifically, refers to garments that are placed against or in proximity to the body of the wearer to absorb and contain various exudates discharged from the body. A non-exhaustive list of examples of absorbent articles includes diapers, diaper covers, disposable diapers, training pants, feminine hygiene products, and adult incontinence products. The term "disposable absorbent garment" refers to absorbent garments that are intended to be discarded or partially discarded after a single use (i.e., they are not intended to be laundered or otherwise restored or reused).

The present invention can be used with all of the foregoing classes of absorbent articles, without limitation, whether disposable or otherwise. These classifications are used interchangeably throughout the specification, but are not intended to limit the claimed invention. The invention will be understood to encompass, without limitation, all classes and types of absorbent articles, including those described above.

In the context of absorbent article manufacturing equipment and machines, the term "machinery component" or "component" can refer, but are not limited, to any part of a machine, such as shafts, gears and other speed adjustment devices; motors, drives and other power equipment; electrical, electronic and electromechanical devices such as computers, programmable controls, feedback devices, sensors and the like; and processing equipment such as conveyors, cutters, folders, adhesive applicators and so on. In the context of absorbent articles themselves, the term "component" can refer, but is not limited, to designated selected regions, such as edges, corners, sides or the like; structural members, such as elastic strips, absorbent pads, stretchable layers or panels, layers of material, or the like; or a graphic. The term "machine-direction" or "MD" refers to the primary direction of movement of continuously moving layers, continuous assemblies or discrete assemblies in the production line, and the term "cross-direction" or "CD" refers to a direction transverse to the machine-direction.

The following detailed description is made in the context of incorporating graphics, such as decorative graphics, instructional graphics, wetness indicators and the like, into absorbent articles, and specifically a baby training pant. Preprinted rolls of graphics and complex control systems that require the use of reference markers and the like are not required to accurately incorporate the graphics at the desired location in the absorbent articles.

In a preferred embodiment, graphics are incorporated in to absorbent articles by using a printer to print a series of graphics onto a moving substrate that is eventually divided and placed into absorbent articles. The graphics are printed at the proper spacing by sensing a line speed reference signal from a target machinery component, and rotating the printer's print cylinder at a predetermined speed based on the line speed reference signal. The phase of the graphics, which dictates where they appear in the final absorbent article, is controlled by sensing a phase difference signal from a machinery component and setting the print cylinder phase angle, based on the phase difference signal, to approximate a predetermined phase angle that is pre-determined to properly locate the graphics.

The present invention provides absorbent articles having graphics accurately positioned with respect to other components of the absorbent article. Examples of graphics include, but are not limited to: indicia highlighting or emphasizing leg and waist openings in order to make product shaping more evident or visible to the user; indicia highlighting or emphasizing areas of the product to simulate functional components such as elastic leg bands, elastic waistbands, and fly openings; indicia highlighting areas of the product to change the appearance of the size of the product; functional graphics such as wetness indicators, temperature indicators, fit indicators, and the like; front and/or back labels or pictorials; or written instructions. All of these graphics may comprise decorative graphics that are intended to improve the look of the garment.

With reference to FIG. 1, an assembled training pant 10 according to the present invention comprises a front waist panel 10a, a rear waist panel 10b opposite the front waist panel 10a, and a crotch portion 10c located therebetween. The sides of the shown training pant 10 comprise elastic side panels 18. However, in an embodiment of the invention suitable for use as a diaper, the elastic side panels 18 may be replaced by elastic or inelastic fasteners, such as tapes or hook-and-loop fasteners. Of course, other configurations are also possible.

Figure 2:
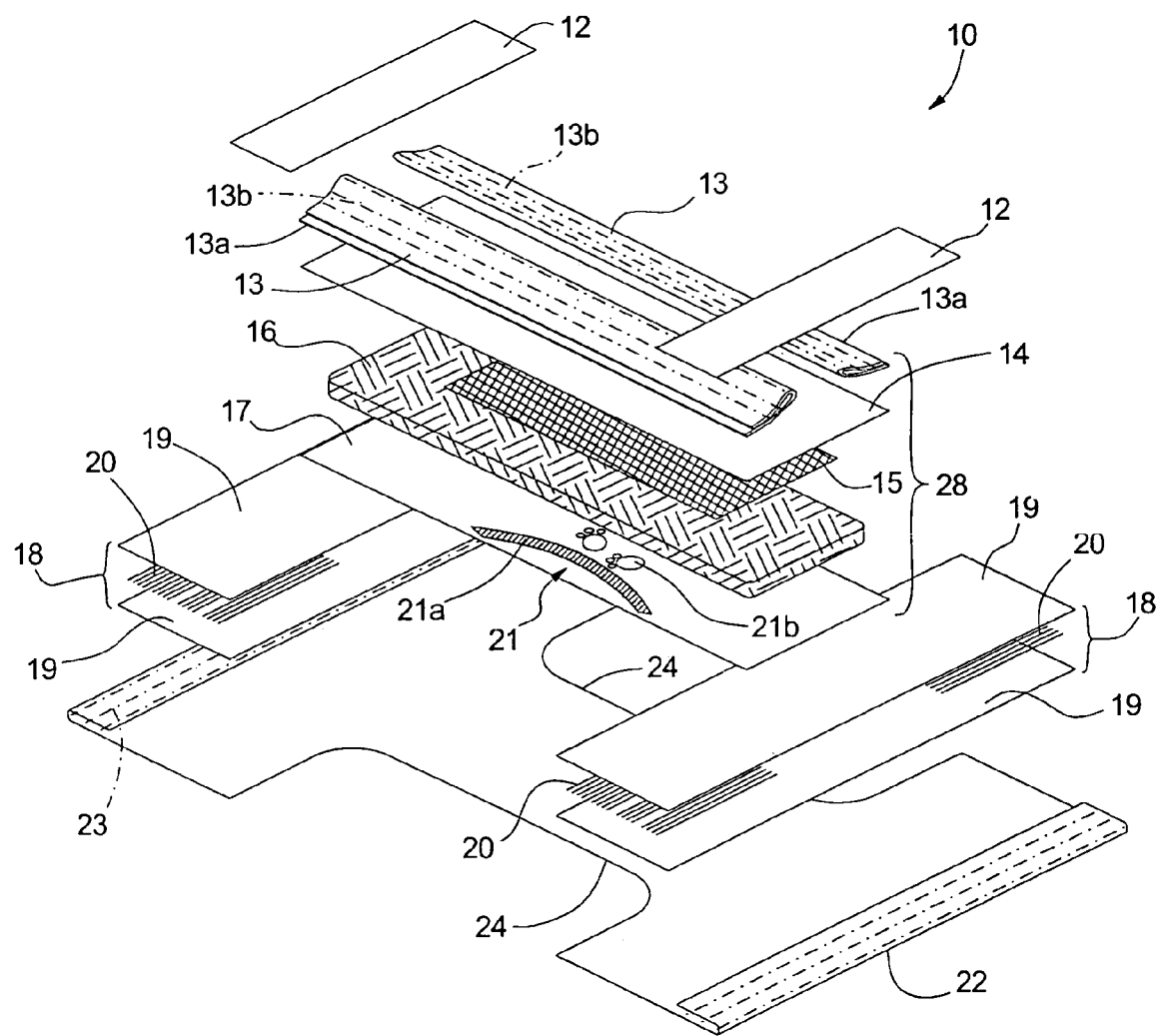
FIG. 2 is an exploded view of the training pant of FIG. 1.

Referring to FIG. 2, which is an exploded view of the garment of FIG. 1, shown separated at its side seams and laid flat, the training pant 10 is provided with an absorbent pad 16 positioned between a liquid impermeable backsheet 17 and a liquid permeable topsheet 14. The training pant 10 further includes an outermost non-woven layer 22 having a cloth-like texture and elastic side panels 18 positioned between the liquid impermeable backsheet 17 and the outermost non-woven layer 22 in order to provide elasticity thereto.

The training pant 10 also comprises a graphic 21. The graphic 21 generally includes a functional and/or visually pleasing design or pattern or, as shown, a combination of designs, and is applied to the absorbent article during manufacturing such that it is located at a designated area in the final absorbent article 10. The graphic 21 may comprise a combination of a wetness indicator 21a and a decorative graphic 21b, but either may be used alone or in different combinations. The wetness indicator 21a portion of the graphic 21 comprises a fluid-sensitive material that smears, changes color, dissolves or becomes translucent when exposed to bodily fluids. It has been found that such wetness indicators 21a can be readily seen from outside the garment through the thin backsheet 17 and non-woven layer 22 (see FIG. 2) and any other intervening layers. Dyes suitable for creating a wetness indicator are known in the art, and described, for example, in U.S. Pat. No. 5,130,290 to Tanimoto, U.S. Pat. No. 6,297,424 to Olson et al. and U.S. Pat. No. 6,307,119 to Cammarota et al., which are incorporated herein by reference. The decorative graphic 21b comprises any suitable fluid resistant dye, as are known in the art. Although the graphic 21 of FIG. 1 is shown in the crotch portion 10c, it may be placed in other locations, as desired by the product designer. Multiple graphics in different locations also may be used.

The liquid impermeable backsheet 17 can preferably be formed from polyethylene, however any suitable material can be used, as is known in the art. In a preferred embodiment, a graphic 21 is positioned on the inside-facing surface of the backsheet 17. This position is particularly preferred if the graphic 21 is a wetness indicator. Of course, the graphic also may be placed on the outside-facing surface of the backsheet 17. The outermost non-woven layer 22 may also include at one or more graphics (not shown) positioned on the inner or outer surface thereof.

The absorbent pad 16 preferably comprises a mixture of cellulosic fibers, such as comminuted softwood pulp fibers, and distributed particles of a superabsorbent polymer (SAP). The pulp/SAP absorbent core is also preferably surrounded by a tissue layer over-wrap (shown schematically at 16' in FIG. 6A) to contain the SAP. However, it should be recognized that any absorbent material known in the art could be used.

The topsheet 14 is preferably made from any suitable material known in the art, including polymeric fabrics such as polyolefin non-woven fabrics. Common polyolefin non-woven fabrics include polypropylene and polyethylene spunbonded fabrics. Additionally, the topsheet of the present invention can be formed from non-woven bicomponent polymeric fabrics or an apertured film material.

The training pant may also include a transfer layer 15 adjacent the absorbent pad 16, as well as leg gathers 13. The leg gathers 13 may comprise leg gather elastics 13b placed between folded non-woven ribbons 13b, or have any other suitable construction, as known in the art. Non-woven end strips 12 are positioned at the longitudinal ends of the discrete absorbent core assembly 28 (which in this embodiment comprises the topsheet 14, absorbent pad 16, backsheet 17, transfer layer 15 and leg gathers 13, but may comprise other varieties of components) to help hold the parts in place and prevent them from peeling away from the outer non-woven layer 22. The end strips 12 also may be partially unattached at their edges closest to the absorbent pad 16 so that they tend to rise up and help impede the longitudinal flow of body exudates.

The elastic side panels 18 preferably comprise a composite of elastic elements 20 and carrier strips 19. During production, the elastic elements 20 extend entirely across the width of the waist opening. However, the elastic elements 20 may be cut, causing them to snap back to the side edges of the article corresponding to the area where the elastics have been adhesively attached to the carrier strips 19. In this manner, the elastic elements 20 are positioned and cut such that they do not overlap the graphic 21 and provide a smooth and aesthetically-pleasing outer surface. The elastic elements 20 are shown cut in this manner in FIG. 2. The training pant 10 may also include elastic waist elements 23 that encircle the wearer's waist, and elastic leg elements (not shown) extending along the leg openings 24 to encircle the wearer's legs. Waist and leg elastic elements are known in the art.

Figure 3:
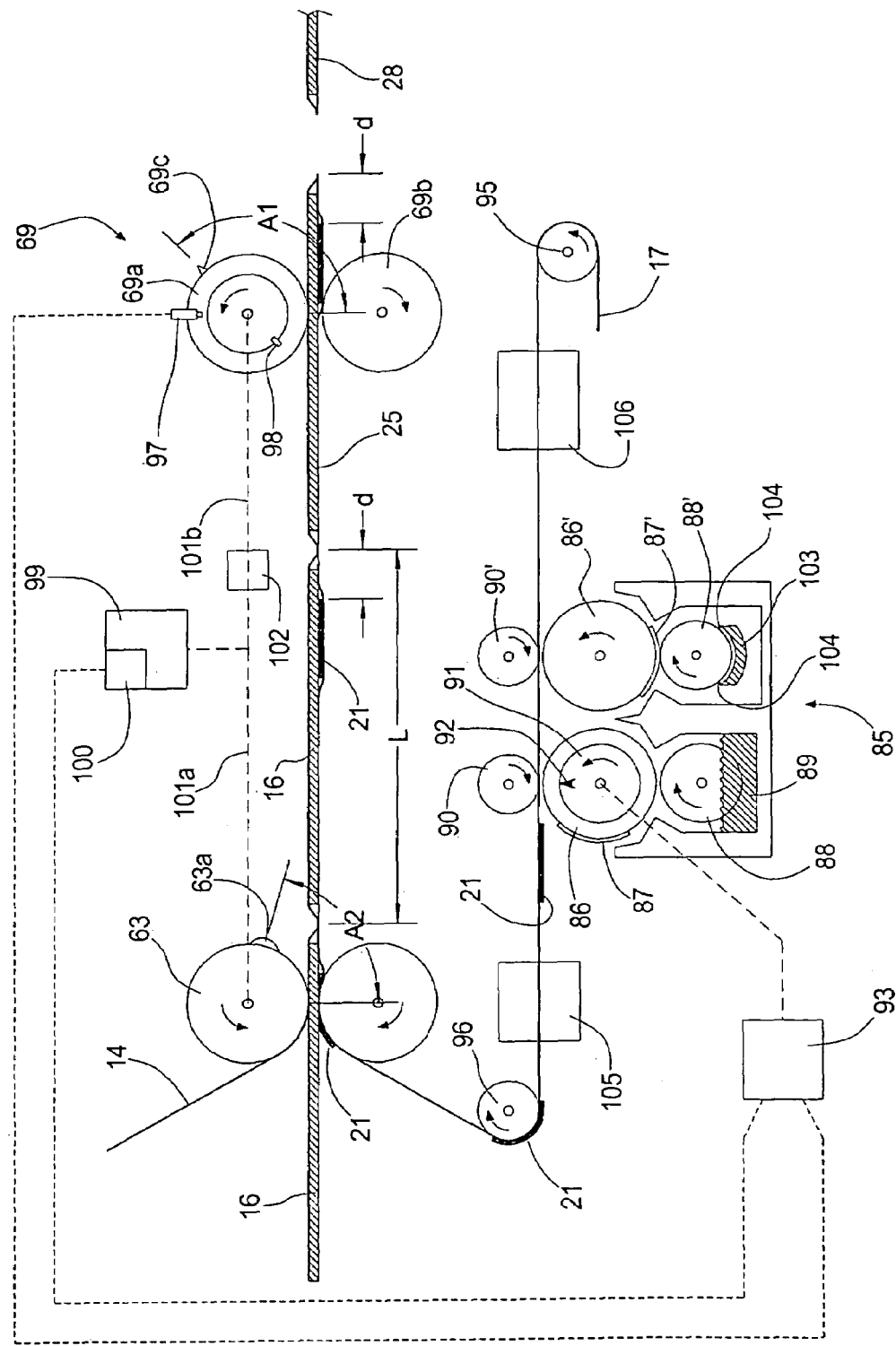
FIG. 3 is a schematic of a preferred manufacturing line for incorporating a graphic on an absorbent article.

A preferred embodiment of the present invention is now described with reference to FIG. 3. FIG. 3 depicts a portion of an absorbent garment assembly line in which a continuous supply of absorbent pads 16, a topsheet material web 14 and a backsheet material web 17 are joined together at a sealer 63, such as a side seal compression roll or perimeter sealer, to form a continuous core assembly 25. Sealer 63 may comprise any type of sealer, such as heat sealer or, preferably, a pair of press rolls that operate in conjunction with adhesive applicators (not shown) and compress the assembly to help set the adhesive bonds between the assembly components. It will be appreciated that the topsheet 14, backsheet 17 and/or pads 16 may be assemblies of various parts. For example, the topsheet 17 may be a topsheet assembly layer 27 comprising various additional components, as described elsewhere herein with respect to FIGS. 5 and 6A. The continuous core assembly 25 is conveyed to a cutter 69, that cuts the continuous core assembly 25 into discrete absorbent cores 28. The discrete absorbent cores 28 are then assembled into absorbent articles 10, such as those in FIGS. 1 and 2, as described elsewhere herein, particularly with reference to FIGS. 5 through 6C.

According to a preferred embodiment of the invention, graphics 21 are incorporated into the continuous core assembly 25 by printing them on the backsheet 17. In an embodiment in which the graphics 21 comprise a wetness indicator, it is preferred to print them on the inside-facing surface of the backsheet 17 (i.e., the surface that ultimately faces the absorbent pad 16 and the wearer during use), so that urine or other body fluids can contact and react with the graphic 21. It will be appreciated that in other embodiments, the graphic also may be printed on the outside of the backsheet 17, the topsheet 14, or on any other layer of material that is ultimately incorporated into the absorbent article 10.

The graphics 21 are printed on the backsheet web 17 at a predetermined distance frequency. The term "predetermined distance frequency" means that each graphic 21 is printed on assembly at such a distance from the previous and next graphic 21 (i.e., distance frequency) that they are spaced along the length of the assembly by an appropriate predetermined distance to result in the placement of a single graphic 21 on each final product. For instance, the graphics 21 can be spaced along the length of the backsheet web 17 at a predetermined distance that generally corresponds to the length of the discrete absorbent core assembly 28, such that a single graphic 21 is located on each core assembly 28, and thereby one on each article 10, as depicted in FIGS. 1 and 2. Alternatively, if multiple graphics 21 are desired for each article, then the predetermined distance frequency is selected so that the desired multiple of graphics 21 are on each final product.

The graphics 21 may be printed by any suitable method, such as offset printing, gravure printing, flexographic printing, photostatic printing and the like. Flexographic offset printing is preferred. A preferred printer 85, depicted FIG. 3, is an offset flexographic printer having a print cylinder 86, flexographic printing plate 87, inking roll (anilox) 88 and impression roll 90. The printing plate 87, which bears the desired printing pattern, is attached to the print cylinder 86 by magnetic attachment, adhesive attachment, or any other suitable attachment technique, as will be appreciated by those skilled in the printing arts. During operation, the print cylinder 86, with printing plate 87 attached, is rotated into contact with the inking roll 88. The inking roll 88 receives ink from an ink source, such as an inkwell 89, and deposits a coating of ink onto the raised print pattern of the printing plate 87. The print cylinder 86 is then further rotated until the printing plate 87 contacts the backsheet 17, at which point the ink is deposited onto the backsheet 17. The impression roll 90 supports the backsheet 17 as it is being printed. It will be understood that the print cylinder need not be perfectly cylindrical, and may, in fact, not be cylindrical at all, provided it is controllable rotated about an axis, has sufficient structure to support the printing plate 87, and doest not interfere with the substrate upon which it is printing.

Although the printer 85 may have a single print cylinder 86 (as in FIG. 6A), the printer 85 of FIG. 3 is shown having an optional second print cylinder 86' and its associated printing plate 87', inking roll 88' and impression roll 90' (in some embodiments, the print cylinders 86, 86' may share a common impression roll 90, inkwell 89 or other components). Inking roll 88' is shown as an alternative preferred embodiment in which inking roll 88' receives ink from an adjacent ink chamber 103 having doctor blades 104 that meter the amount of ink deposited into inking roll 88'. Such devices are available from Bell-Mark of Pine Brook, N.J. By using two print cylinders 86, the embodiment of FIG. 3 is capable of simultaneously printing two separate graphics 21 having different colors or ink properties, such as a wetness indicator 21a and a decorative graphic 21b, onto the backsheet 17. The movement of the second print cylinder 86' and its associated devices can be coordinated with that of print cylinder 86 using any known device, such as gears, belts and pulleys, servodrives and so on. A preferred printer for use with the present invention is the TWO COLOR FLEXPRINT II, which is available from Bell-Mark of Pine Brook, N.J.

In a preferred embodiment, the printer 85 is operated in conjunction with a corona treater 106, located immediately before the printer 85, that applies a charge to the backsheet web 17 to improve its printability. It is also preferred to provide a dryer 105, that uses forced air or impingement jets to dry the printed backsheet web 17 immediately after it emerges from the printer 85. Corona treaters and dryers are known in the art.

Stated in general terms, the present invention provides a method and apparatus for printing the graphics 21 as a predetermined distribution frequency on the backsheet 17 (or any other layer) so that they are properly located in the finished product. The proper location of the graphic 21 depends on the overall absorbent article design. For example, in the embodiment of FIG. 3, it is desired to place the graphic 21 a distance d from the end of each discrete absorbent core 28 of the continuous core assembly 25. Distance d is selected, for example, so that the graphic 21, which is a combined wetness indicator 21a and decorative graphic 21b, as shown in FIGS. 1 and 2, is positioned near the crotch 10c of the garment where urine from a male user is likely to strike the graphic 21.

In a preferred embodiment, the present invention controls the printer 85 to print the graphics 21 using two primary inputs: a line speed reference signal that indicates the operating speed of the machinery, and a phase difference signal that indicates the phase difference (i.e., relative angular position) between the printer and a target component on the machinery. The line speed reference signal is used to operate the printer 85 at the same speed as the rest of the machinery, as measured by the rate of product manufacture (products per minute), to thereby print graphics 21 at the proper predetermined distribution frequency on the backsheet web 17. The phase difference signal is used to operate the printer 85 at the proper phase relative to the machinery and thereby position the graphics 21 in the proper location on each absorbent article 10 produced by the machine. It has been discovered that these two inputs are sufficient to provide a high-speed continuous supply of properly printed absorbent articles 10 without requiring feedback control systems to continuously measure the location of the graphic 21.

The first input, the line speed reference signal, is used to operate the printer 85 at the same product speed as the rest of the machinery. The particular machinery component (or components) that is providing the line speed reference signal is referred to herein as the "line speed target component," and the instantaneous speed at which the line speed target component is operating is the "target speed." When multiple line speed reference signals are used to provide the line speed reference signal, an average or other mathematical derivation of the signals may be used. The "product speed" is the rate at which the machinery is making products, which is typically expressed in terms of products per minute, or "PPM."

Figure 6A:
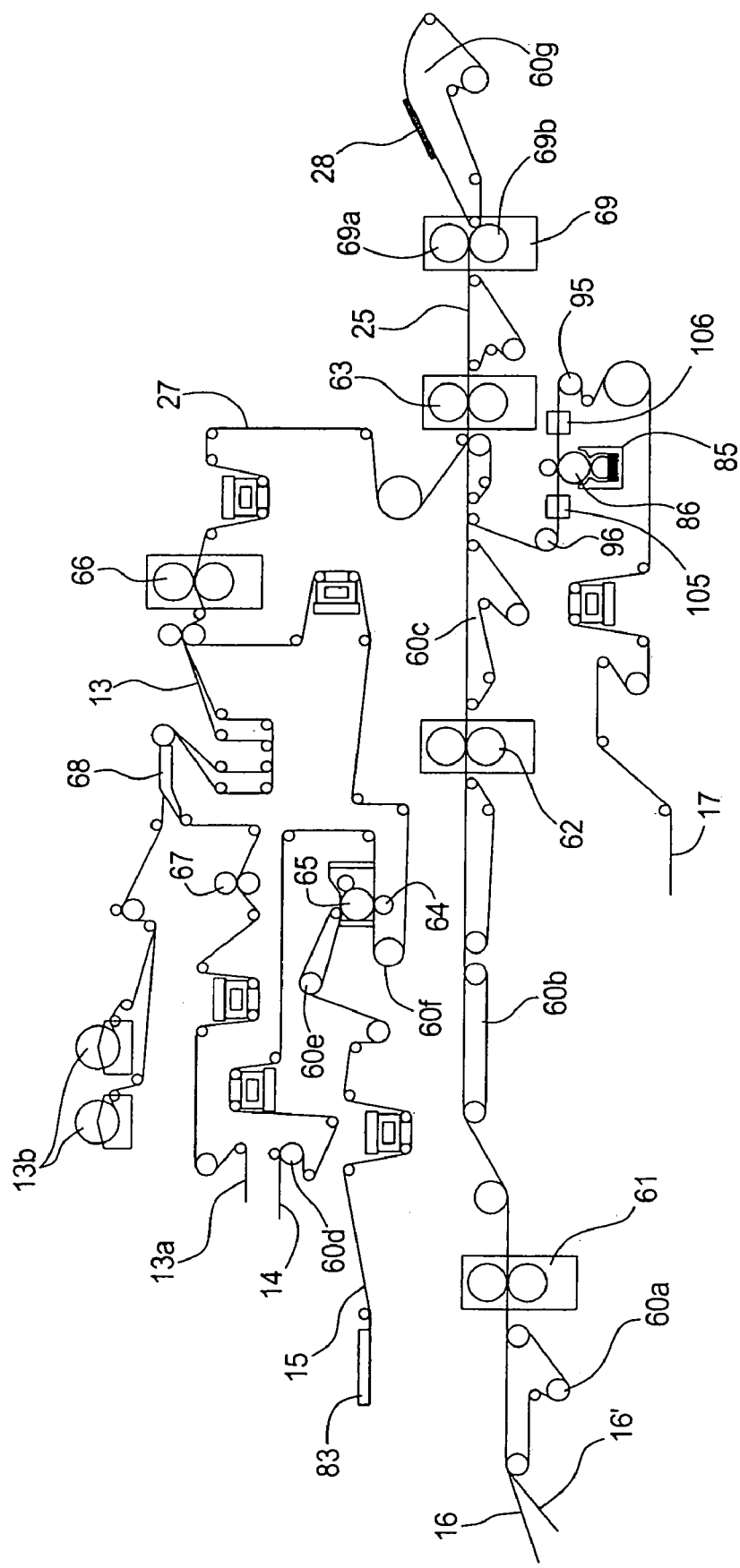
FIGS. 6A–6C show a schematic of a preferred manufacturing line for practicing the invention according to the preferred embodiments.

It will be appreciated that the actual linear and angular speeds of the various machinery components may vary along the length of the machine, even though they all might be operating at the same PPM. For example, in an embodiment in which a continuous supply of absorbent pad material 16 is wrapped in a tissue 16', cut, and spaced apart for insertion between the backsheet 17 and the topsheet 14, the various conveyors that move the absorbent pad 16 may operate at different speeds to account for "draw" (stretching) of the pad 16 and tissue 16', and to space the individual absorbent pads 16 from one another. Such an embodiment is shown in FIG. 6A, and described in more detail elsewhere herein. In this embodiment, conveyor 60a may operate at a first linear speed (e.g., 500 feet per minute ("fpm")), while conveyor 60b operates at a slightly faster linear speed (e.g., 510 fpm) to maintain tension on the absorbent pad 16/tissue 16' assembly, which stretches as it is pulled. The speed difference reveals the amount of "draw" between the two points, which in this case would equal 2% (i.e., (510 fpm–500 fpm)/500 fpm); this is the amount the material stretches during manufacture between conveyor 60a and conveyor 60b. Meanwhile, conveyor 60c may operate at an even greater linear velocity (e.g., 550 fpm) to space the severed discrete absorbent pads 16 apart from one another so that they are placed in the appropriate location between the topsheet 14 and backsheet 17. It will be understood, however, that all of these conveyors are operating at the same product speed, as measured in products per minute PPM.

The line speed reference signal is used to match the printer's speed (in PPM) with the rest of the machinery. In a preferred embodiment, the printer controller 93 detects the line speed target component's target speed via the line speed reference signal and uses this value to a determine the desired printer speed that will cause the printer 85 to operate at the same PPM as the line speed target component, and therefore the rest of the machinery. Preferably, the printer controller 93 is programmed with a simple proportional relationship between the target speed and the printer speed. This can be accomplished by evaluating the relative speeds at which the line speed target component and printer 85 operate to achieve the same PPM.

Many components on absorbent article manufacturing lines have a fixed proportional relationship between their operating speed and the machine's PPM. These components provide the simplest linearly proportional (i.e., speed-independent) relationships between the target speed and the printer speed. For example, conveyor 60a, as described in the previous example, may produce 412 PPM when it operates at 500 feet per minute (fpm), and this ratio (412/500=0.824 PPM/fpm) is generally fixed regardless of the speed of operation. The relationship between the operating speed of conveyor 60a and the PPM is more preferably represented as a function of the angular velocity of the machinery that drives conveyor 60a. For example, conveyor 60a may be driven by a 6 inch diameter sprocket, which rotates at a speed of 318.35 rpm (500 fpm/(π×0.5 feet/revolution)) to drive conveyor 60a at 500 fpm and the machine at 412 PPM. Using angular velocity (rpm), rather than linear speed, the measure of PPM as a function of angular velocity is 1.294 PPM/rpm (412 PPM/318.35 rpm), or, more simply, 1.294 parts/sprocket revolution. These simple proportional relationships can be calculated based on any other component of the machinery, including the printer 85, that operates at PPM speeds that are essentially linearly proportional to the component's angular speed. Furthermore, more complex mathematical relationships can be determined for components that operate at speeds that are not linearly proportional to the machine's PPM output, and therefore such components may also serve as the line speed target component and provide the line speed reference signal to the printer controller 93.

Once these relationships are established, it is apparent that the printer controller 93 should be operated according to the equation:

$$\frac{\text{Printer}}{\text{rpm}} = \frac{\left(\frac{\text{\# parts}}{\text{target revolution}}\right)}{\left(\frac{\text{\# parts}}{\text{printer revolution}}\right)} \times \frac{\text{Target}}{\text{rpm}}$$

This equation provides the predetermined speed, relative to the line speed reference signal, at which the printer 85 should be operated. Using the above example, if the printer 85 operates at 2 parts/printer revolution (i.e., the printer 85 prints two graphics 21 per revolution), and the sprocket operates at 1.294 parts/sprocket revolution, then the printer controller 93 should be programmed to operate the printer 85 at 0.647 printer revolutions/sprocket revolution to match the PPM rate of the sprocket. Alternatively, if the printer 85 prints one graphic per revolution (1 part/printer revolution), then the printer controller 93 would operate the printer 85 at 1.294 times the speed of the sprocket to maintain the same PPM rate as the rest of the machinery. In cases in which the line speed target component's speed is not linearly proportional to the PPM rate of the machine, the above equation can still be used to generate the predetermined speed of the printer 85 relative to the line speed reference signal, by replacing the numerator (# parts/target revolution) with the mathematical relationship that defines the target speed-to-PPM relationship. Other mathematical derivations also may be used to obtain the predetermined speed of the printer 85 relative to the line speed reference signal.

The line speed reference signal of the machinery is preferably provided as an angular velocity. Angular velocity measurements are easily obtained using a hall-effect or any other type of encoder that creates a number of electrical pulses for each revolution of the shaft. Such encoders are known in the manufacturing arts, and these, or any angular velocity measuring equipment, may be used with the present invention. The angular velocity of the line speed target component also may be internally measured by an encoder that is integrated into the drive motor that operates the line speed target component. Other types of device, such as mechanical or electromechanical tachometers and the like, also may be used to generate the line speed reference signal, as will be understood by those of ordinary skill in the art.

In a preferred embodiment, shown in FIG. 3, some or all of the components of the manufacturing line are driven by a drive 99 having an internal encoder 100 that monitors the drive's angular velocity. In the embodiment of FIG. 3, the drive 99 operates both the sealer 63 and the cutter 69 through multiple drive paths 101a, 101b. Each drive path 101a, 101b may comprise a series of shafts, belts and pulleys, gears and the like, or may simply comprise a direct (i.e., 1-to-1 speed) connection between the main drive 99 and the machinery components. These drive paths 101a, 101b dictate the relationship between the angular velocity of the main drive 99 and the PPM of the machine, as will be understood by those of ordinary skill in the art. In this embodiment, the line speed target component may comprise the main drive 99, the cutter 69 and/or the sealer 63, and the line speed target component speed may be measured by the main drive's internal encoder 100, or a stand-alone encoder 102 mounted on the cutter drive path 102b or the heat sealer drive path 102a. The stand-alone encoder 102 also may be mounted directly to the cutter 69 or sealer 63. The encoder 101 or 102 generates a line speed reference signal that is sent to the printer controller 93.

It should be noted that certain machinery components are required to operate at angular speeds, as measured by rpm, that are essentially exact multiples or divisors of the PPM speed. This is true for most components that provide an identical, discrete operation on each product (called "unitary" operations). The components that perform such operations are referred to herein as "unitary" components. For example, if the cutter 69 has a single knife 69c, then it must be rotated one revolution for each product, otherwise the absorbent cores 28 will not be cut to the proper length. As such, the PPM to rpm ratio for the cutter 69 is required to be 1-to-1. Similarly, if the cutter 69 has two knives, then it must be operated at ½ revolution per product, yielding a PPM to rpm ratio of 2-to-1 (i.e., two products per cutter revolution), and so on. Furthermore, in many cases it is desirable to match the linear velocity of the operative surfaces of such unitary manufacturing components with the linear velocity of the assembly that is being manufactured to prevent damage to the assembly. The linear velocity of the operative surfaces of the component are most easily matched to the linear velocity of the assembly by matching the circumference of the component to the length of the product. This can be done by having the component's circumference equal the product length or a multiple or divisor thereof. For example, the cutter 69 of FIG. 3 has a single knife 69c, and cuts one discrete absorbent core 28 from the absorbent core assembly 25 per revolution. As such, the circumference of the cutting drum 69a is selected to be approximately equal to the length L of the discrete absorbent core 28.

Of course, certain exceptions exist to the general requirement to match the linear velocity of the manufacturing components to that of the assembly, such as cut-and-space vacuum conveyors or other spacing operations, as will be understood by those of ordinary skill in the art. Furthermore, in contrast to the unitary devices described immediately above, devices that do not perform unitary operations can have virtually any diameter, and can operate at any angular velocity, provided the linear speed of the surface of the device is selected so that it does not damage the assembly. For example, the cutter's anvil drum 69b, which may be a simple smooth surface, can have any diameter, provided its surface speed is matched with that of the absorbent core assembly 25 (this would not be the case if the anvil drum 69b had a discrete surface, such as a knife pad, for engaging with the knife 69c).

Like the cutter 69, the printer 85 performs a unitary operation and the printer's rpm must be the same as, or a multiple or divisor of, the machine's PPM. Also, in order to ensure that the printer 85 does not damage the backsheet 17, the print cylinder 86 is preferably selected so that its effective circumference is equal to, or a multiple or divisor of, the backsheet length L. In the embodiment of FIG. 3, the backsheet 17 has the same length. L as the discrete absorbent cores 28.

It should be noted that the backsheet material web 17 may stretch between the printer 85 and the sealer 63 or cutter 69. In this case, the effective circumference of the print cylinder 86 should be reduced in size to account for the fact that the backsheet material is not as stretched when it passes through the printer 85 as it is when it is in the absorbent core assembly 25. For example, if the backsheet web 17 is only 98% as long when it passes though the printer 85 as it is when it is incorporated into the absorbent core assembly 25, then the print cylinder's effective diameter should be reduced to equal 98% of the final backsheet length L.

Although such corrective sizing is possible, it has been found that problems associated with backsheet stretch can be reduced to manageable levels more simply by minimizing the stretch of the backsheet material 17 between the printer 85 and the cutter 69 using conventional stretch-reducing methods (once the backsheet 17 reaches the cutter 69 it is severed and no longer subject to substantial stretching that could cause the graphic 21 to be mislocated). For example, the stretch of the backsheet material 17 can be minimized or eliminated by operating the printer 85, sealer 63, cutter 69 and any intervening conveyors at approximately the same linear speed. Stretch can also be reduced by minimizing the total distance between these components. Draw points 95 and 96, such as those shown in FIG. 3, can be used to monitor the backsheet stretch by measuring the relative speeds of the backsheet web 17 at various points, and identify when problematic conditions arise. Using these methods, it is important have accurate web speed control, which can be accomplished by using multiple drive point speed controls, as are known in the art.

In a preferred embodiment, the print cylinder 86 has a single flexographic printing plate 87, and the print cylinder's effective circumference is equal to the backsheet length L. However, various other combinations of print cylinder sizes and printing plates 87 are available with the present invention. For example, if a single graphic 21 is applied by each print cylinder 86, then the print cylinder's circumference should approximately equal the backsheet length L or be a multiple thereof. If the print cylinder circumference equals the backsheet length L, then the print cylinder should have one print plate 87 and rotate once per product. If the print cylinder circumference equals a multiple of the backsheet length L, then the print cylinder should have that multiple of evenly-spaced printing plates 87 and rotate once per that multiple of products. Also, if each print cylinder 86 is required to print multiple evenly-spaced graphics 21 on each garment (such as identical front and rear patterns), then the print cylinder may have a single printing plate 87 with the desired repeated pattern, and have a circumference equal to a divisor (e.g., ½) of the backsheet length L. The print cylinder circumference also may be twice the backsheet length L, and may have two different printing plates 87 with different graphics thereon. In such a case, the print cylinder 86 may operate at an rpm selected to be half the PPM speed so that the two different printing plates 87 print an alternating pattern of graphics 21 on successive backsheets 17 to create a variety pack of absorbent articles 10. As another example, the print cylinder circumference may be equal to the backsheet length L, and may rotate once per product, but the print cylinder 86 may have multiple printing plates 87 that print different graphics 21 on different parts of the backsheet 17. Other variations of print cylinder circumference and printing plate combinations will be readily apparent to those of ordinary skill in the art from the teachings herein.

The "effective circumference" of the print cylinder 86 may be calculated at the print cylinder surface, or more preferably at the raised printing surfaces of the printing plate 87. When a flexographic printer is used, the printing plate 87 comprises a flexible material that may compress as it interacts with the impression roll 90, in which case it may be preferable to calculate the print cylinder's effective circumference based on the distance between the center of the print cylinder 86 and the nearest point on the impression roll 90, which corresponds to the height of the raised printing surfaces of the printing plate 87 as they are compressed when pressed against the impression roll 90 during actual printing. Although these calculations may allow the print cylinder 86 to be manufactured to have an effective circumference that is very nearly identical to the backsheet length L, some variance may still exit, in which case the print cylinder 86 may move slightly faster or slower than the backsheet material web 17, which is driven by a separate drive (not shown). However, some variance is acceptable, and damage from such variances is mitigated or eliminated by the fact that the printing plate 87 only contacts the backsheet 90 for a portion of the print cylinder's rotation, allowing any stretch or compression of the backsheet web 17 to be relieved between prints.

The printer controller 93 that drives the print cylinder(s) 86 preferably comprises a conventional programmable-logic servodrive device, although other suitable control devices may be used, as known in the art. In a preferred embodiment, the printer 85 comprises a Two COLOR FLEXPRINT II (available from Bell-Mark of Pine Brook, N.J.), which has a self-contained servodrive power system. Other suitable servodrives are known in the art. While the printer controller 93 may comprise programmable circuitry within the servodrive itself, it is also anticipated that the printer controller 93 may comprise circuitry that operates entirely or partially externally of the servodrive, such a separate programmable logic controller (PLC), such as are known in the art.

A user programs the proper printer speed-to-target speed ratio or equation into the printer controller 93 based on the relationships of their drive speeds to the PPM of the machine, as such relationships are described elsewhere herein. The printer controller 93 uses conventional algorithms to receive the line speed reference signal from the line speed target component, calculate the appropriate printer speed, and drive the printer 85 at that speed. The printer controller 93 "locks" the printer speed to the line speed reference signal so that it follows any fluctuations in the line speed. Various feedback or feed-forward algorithms may be employed to optimize the process of following the line speed reference signal. The printer controller 93 also may use various algorithms to filter noise, minimize lag time, and improve the robustness of the control system. These and other useful algorithms are known in the art.

Although many different machinery components may be the line speed target component, it is preferred that the line speed target component is a drive that has its own encoder 100, such as the main drive 99 described herein. This embodiment helps reduce the cost of the system by using existing angular speed measuring equipment. It is alternatively preferred that the cutter 69 is the line speed target component having its own stand-alone encoder 102 mounted thereon. Both the printer 85 and the cutter 69 are unitary components that operate at rpm speeds that are equal to, or multiples or divisors of, the PPM speed. As such, using the cutter 69 as the line speed target component simplifies the printer speed-to-target speed calculation. Furthermore, since whole numbers are involved in this unitary-to-unitary conversion (e.g., 1-to-1, 2-to-1, etc.), this reduces or eliminates mathematical roundoff errors that may accumulate during long continuous production runs and result in noticeable product defects. Of course, these two embodiments may be combined in an embodiment in which the cutter 69 is driven by its own dedicated drive that has an internal encoder. Using the embodiments of the invention described herein, the printer 86 can be effectively operated at a speed that places the graphics 21 at the desired predetermined distance frequency on the backsheet web 17, such that the desired number of graphics 21 are printed for each absorbent article 10 produced by the machinery.

While the printer controller 93 can use the line speed reference signal to print the proper number of graphics 21 per article, this does not guarantee that the graphics 21 will be printed at the desired location on the articles. The second signal used by the printer controller 93, the phase difference signal, is used to ensure that the graphics 21 are properly located. For example, the phase difference signal is used to place the graphics at distance d behind the end of each discrete absorbent core 28, as shown in FIG. 3.

The majority of machinery components in a typical manufacturing line operate at speeds that have a fixed relationship with the overall machine speed, and when the machine slows and stops, so do the machinery components. As such, the operation of the various machinery components can be coordinated by permanently indexing them relative to one another. For example, in the embodiment of FIG. 3 the machinery includes a sealer 63 that has an end sealing bump 63a that seals the topsheet 14 to the backsheet 17 between each discrete absorbent pad 16. Sealer 63 also preferably has a cutout that prevents the absorbent pads 16 from being unduly compressed during the sealing operation. The machinery also has a cutter 69 having a knife 69c that cuts the discrete core units 28 at the location at which they are sealed by the end sealing bump 63a. As such, the knife 69a and end sealing bump 63a must be timed, relative to one another (i.e., "phased") to strike the same portion of the assembly. In the example of FIG. 3, the phase angle between the end sealing bump 63a and the knife 69a is the difference between the angles A1 and A2. Since the knife 69 and sealer 63 always operate at speeds that are proportional to the overall machinery speed their movements are "locked" to one another, and their relative phase angle remains constant at all speeds, even when the machinery is stopped. The phase angle is set by indexing (i.e., physically rotating) the two components when the machinery is at a standstill. Once indexed, the cutter 69 and sealer 63 remain at the desired phase angle, regardless of machinery speed, until re-indexed.

Unlike other typical machinery components, however, the printer 85 continues to rotate when the rest of the machinery is shut down. This is required in typical roller-type printers to prevent the ink from drying in the inkwell 89, on the inking roll 88 or on the printing plate 87. In order to continue rotating during shutdown, the printer 85 disengages from the assembly, such as the backsheet web 17, on which it was printing when the printer controller 93 detects that the line speed reference signal has dropped below a predetermined threshold minimum angular speed or PPM speed that indicates the machine's shutdown mode. Disengagement, which is preferably performed automatically by the printer controller 93, may be accomplished by lifting the impression roller 90 and assembly, by moving the inking roll 88 and/or print cylinder 86, or by any other suitable action, as will be readily appreciated by those of ordinary skill in the printing arts. During disengagement the printer controller 93 also "unlocks" the rotation of the print cylinder 86 from the line speed reference signal and operates it at an idle speed selected to prevent the ink from drying. It will be seen that, because the printer 85 is disengaged from the rest of the machinery during the shutdown mode and the print cylinder 86 continues to rotate, the phase of the print cylinder 86 can not be fixed relative to the other machinery components by the same indexing method described above.

It has been discovered that a phase difference signal can be used to overcome the inability to permanently index the print cylinder 86 relative to the rest of the manufacturing line. In general terms, the printer controller 93 uses the phase difference signal to determine the angular position of one of the machinery components, compares this angular position to the instantaneous position of the print cylinder 86 to determine their actual phase difference (i.e., the angle between the printer and the component), and then accelerates (advances) or decelerates (retards) the print cylinder 86 to change the actual phase difference to be equal to a user-defined predetermined phase angle, which is determined as described below. The particular machinery component (or components) that is providing the phase difference signal is referred to herein as the "phase target component," which may comprise any suitable machinery component other than those in the printer 85. The phase target component may be the same as or different from the line speed target component.

The phase difference signal can be generated by any suitable device that detects the phase target component's angular position. Using the present invention, it is only necessary to identify when the phase target component is at a particular position, and it is unnecessary to monitor the track the phase target component's angular position throughout its entire rotation (although this still may be done). As such, the phase difference signal can be generated either by a device that constantly registers the phase target device's angular position, or by a relatively inexpensive unitary device that only generates a signal once per phase target device revolution.

The phase difference signal is preferably generated by a phase target sensor 97 comprising a hall-effect inductance pickup that creates an electrical impulse every time a ferromagnetic phase target marker 98 passes next to it. A preferred phase target sensor 97 is a simple proximity sensor that determines when the target component has passed a certain point on its rotation. Also in a preferred embodiment, the phase target component is the cutter 69, and the phase target marker 98 is mounted to rotate with the cutting drum 69a. In another embodiment, the cutter's knife 69c may act as the phase target marker 98. In the embodiment shown in FIG. 3, the phase target sensor 97 generates a phase difference signal every time angle A3 equals zero. Although it will be seen in FIG. 3 that this position also corresponds to the moment that the knife 69c is cutting the absorbent core assembly 25, this relationship need not be used. Of course, other devices can be used to generate the phase difference signal, such as an encoder, optical sensor, and the like.

When the printer controller receives the phase difference signal, it checks the print cylinder angle at that moment. The print cylinder angle may be determined, for example by placing an encoder 91 on the print cylinder (or the mechanism, such as a servodrive, that drives it) and programming the printer controller 93 to monitor a fixed reference point 92 (such as a zero position) on the encoder and calculate the print cylinder rotation based on the number of encoder pulses that pass after the reference point 92 is detected. For example, if the encoder 91 provides 3600 pulses per revolution, then the print cylinder angle is calculated by counting the number of pulses that have passed since the reference point 92 was detected and dividing by 10. The print cylinder angle also may be determined using a simple proximity sensor (not shown), such as a hall-effect sensor, to provide a reference point, then calculating the angle through which the print cylinder 86 has rotated when the phase difference signal is received, which can be done because the print cylinder angular speed is known. The technology required to receive the phase difference signal and determine the print cylinder angle at the time the phase difference signal is received is known in the art and one of ordinary skill in the art will be able to employ this technology with the present invention without undue experimentation. The print cylinder angle is then checked against the desired predetermined phase angle to determine whether it is within the operating tolerances of the machinery, and if not, which way to adjust it.

Figure 4:
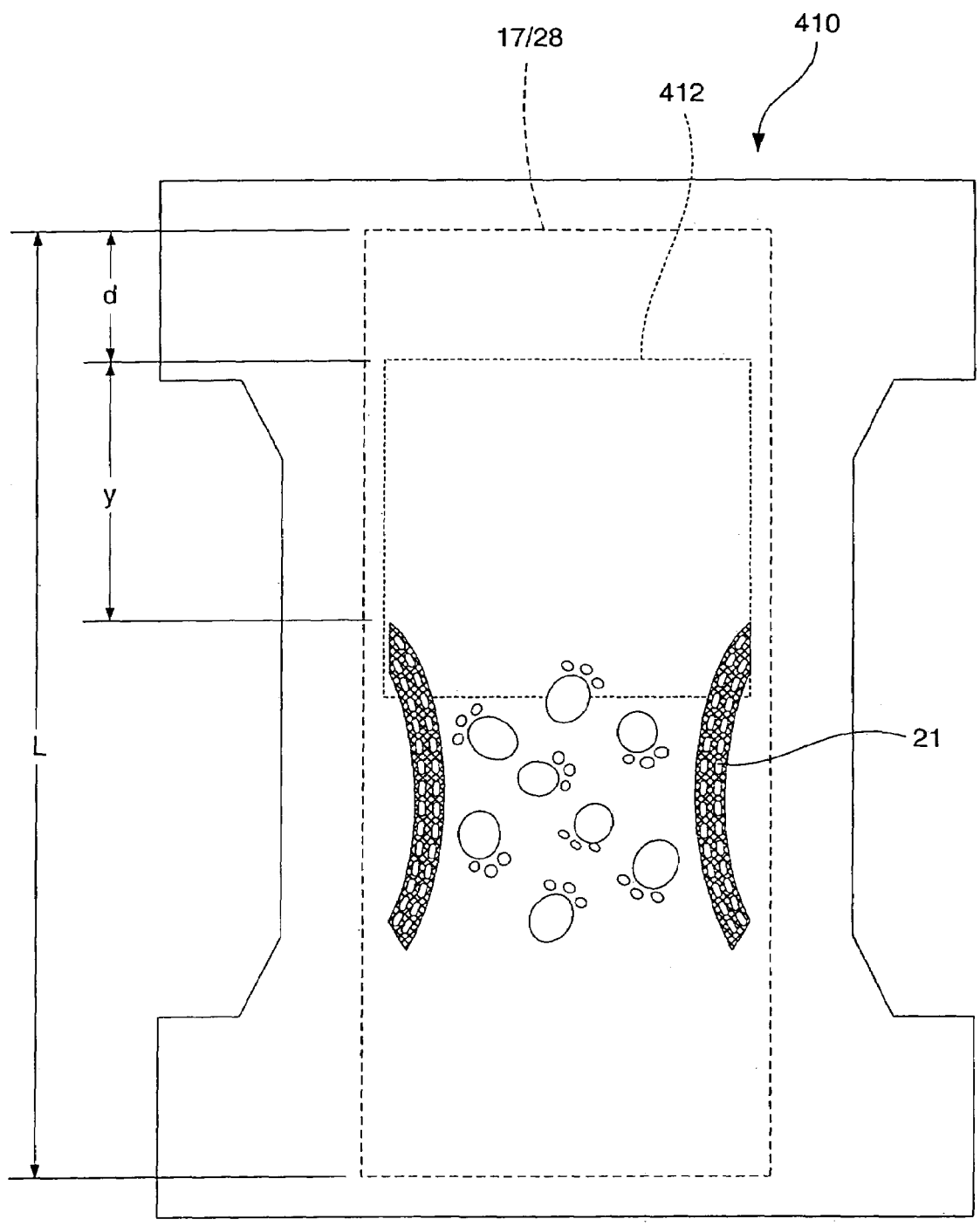
FIG. 4 is a planar view of a test article showing the relevant dimensions required to establish the operating phase angle of the present invention.

The "predetermined phase angle" is the angle at which the print cylinder 86 should be oriented at the time that the phase difference signal is received in order to properly locate the graphics 21 at the desired location on the substrate upon which they are being printed. The predetermined phase angle is determined by an operator without requiring the use of feedback systems in the machinery, and programmed into the printer controller 93. The process for determining the user-programmed predetermined phase angle (the "phasing process") is described now with reference to FIG. 4, which shows a planar view of a test article 410 that is used to determine the proper predetermined phase angle. The phasing process is essentially a simple trial-and-error process that involves operating the machinery, manually comparing the graphics 21 location with the desired location, and calculating the proper operating reference angle. The first step, operating the machinery, should be done long enough to produce a steady-state supply of discrete absorbent cores 28 having the printed graphic 21 thereon. A typical resulting test article 410 is shown in FIG. 4. During the first step, the print cylinder angle is monitored each time the phase difference signal is received and the printer controller 93, and this number is recorded by the printer controller 93 or the operator.

Next, the test article 410 is analyzed to determine how far each graphic 21 is from the desired graphic location 412. In the embodiment of FIG. 4, the desired graphic location 412 is shown at distance d from the leading edge of the backsheet 17. The difference between the desired distance d and the actual location is shown as error distance y. The proper predetermined phase angle can then be calculated by converting the error distance y into an error angle measurement based on the fact that the backsheet length L is equal to one circumference of the print cylinder 86 (if the print cylinder circumference is a multiple of the backsheet length, the angle conversion should be divided by that multiple). If the graphic 21 is located too far forward (the up direction in FIG. 4), then the print cylinder 86 is printing too early relative to the knife cuts and should be retarded by subtracting the error angle measurement from the print cylinder angle that was detected in the first step. If the graphic 21 is located too far back (as shown), then the print cylinder 86 is printing too late relative to the knife cuts and should be advanced by adding the error angle measurement to the print cylinder angle that was detected in the first step.

An example of this calculation is provided for clarity. In this example, the machinery is operated to produce a number of test articles 410 having the graphic 21 located an error distance y of 50 mm behind the desired graphic location 412. The absorbent core length L (and backsheet length) equals 400 mm. During the test run, the print cylinder angle was detected to equal 75 degrees whenever the phase difference signal was received from the phase target sensor 97. As such, when the print cylinder 85 was operating at 75 degrees behind the cutter 69, it was printing 50 mm behind the intended location. The proper predetermined phase angle can now be calculated by first converting the error distance y into an angle measurement, which in this case equals 45 degrees ((50 mm/400 mm)×360 degrees). As such, the print cylinder 86 should be advanced by 45 degrees to eliminate the error distance y, and print the graphic 21 in the desired graphic location 412. Advancing the print cylinder operation by 45 degrees results in the desired predetermined phase angle being 120 degrees (75 degrees+45 degrees). To obtain this angle, the printer controller 93 should be programmed to position the print cylinder 86 at 120 degrees at the moment the phase difference signal is received from the cutter 69. Once the printer controller 93 is operated to obtain the predetermined phase angle for one graphic 21, then the rest of the graphics 21 will also be printed in their respective desired locations because the printer controller 93 reverts to operating the print cylinder 86 according to the line speed reference signal to obtain the desired predetermined distance frequency.

Of course other mathematical manipulations may be used to obtain the same result (e.g., converting angular measurements to linear units, rather than vice-versa, etc.). Furthermore, because the phase between the phase target component and the printer depends on the distance between the two components, this phasing process should be repeated whenever the linear distance between the printer and the phase target component is changed or a different phase target component is selected.

In an embodiment in which the printer 85 has two print cylinders 86, 86', the second print cylinder 86' can be dynamically indexed in a manner similar to that described above for print cylinder 86. More preferably, however, print cylinder 856' is permanently indexed relative to print cylinder 86 as described above with reference to the cutter 69 and sealer 63. Permanent indexing is possible if the two print cylinders 86, 86' are mechanically linked together (such as by gears or belts and pulleys), to always rotate in unison.

In one preferred embodiment, the phase difference signal is only used during startup to dynamically index the print cylinder 86 with the rest of the machinery. In this embodiment, when the line speed reference signal reaches a minimum threshold value (indicating that the machinery is starting), the printer controller 93 initiates a start routine to set the print cylinder phase to the predetermined phase angle and lock the printer speed with the speed of the rest of the machinery. The start routine can operate in any number of ways. For example, the start routine can begin by accelerating the print cylinder 86 from its idle speed and locking the print cylinder speed with the target speed (using the line speed reference signal), and then start comparing the actual phase difference with the predetermined phase angle (using the phase difference signal). If the actual phase difference is less or more than the predetermined phase angle, the printer controller 93 momentarily accelerates the print cylinder 86 so that the actual phase difference is closer to or at the predetermined phase angle, then resumes operating the print cylinder at the desired speed calculated from the line speed reference signal. For simplicity, the term "accelerate" is used herein to encompass both positive accelerations and negative accelerations (i.e., deceleration). Once the print cylinder 86 has obtained the proper phase angle and speed, the printer controller 93 engages the printer 85 with the substrate to begin printing. Other suitable routines will be apparent to those of ordinary skill in the art in light of the teachings provided herein. The startup routine may occur iteratively over the course of several revolutions or may be relatively instantaneous, and may use any conventional control algorithms, as are known in the art. If a servodrive is used to operate the print cylinder, and the startup speed is relatively slow, then this dynamic indexing process can be accomplished almost instantaneously.

In a preferred embodiment, once the printer controller 93 determines that the print cylinder 86 is at the predetermined phase angle relative to the phase target component, the printer controller 93 operates based solely on the line speed reference signal, and does not use the phase difference signal until the next restart. In another embodiment, however, the printer controller 93 can use the phase difference signal throughout its operation as an operational feedback signal to verify that the printer 85 is properly following the line speed reference signal, or that the proper speed relationship is being used between the target component and the print cylinder. Using the phase difference signal as an operational feedback signal may be particularly useful in embodiments in which roundoff error or slight undetected speed variations that are not corrected by the printer controller 93 might cause the printer 95 operate at a slightly different PPM rate from the rest of the machinery, causing slight drifting in the location of the graphics 21.

It has been found that the present invention can accurately print combined wetness indicator/decorative graphics 21 on the inside of a thin polymeric backsheet 17 in a baby training pant 10 as shown in FIGS. 1 and 2 without using complex feedback equipment or systems. Furthermore, the present invention has been able to produce such absorbent articles with a variance in the graphic location of less than about 10 mm in either direction, which is well within tolerable levels of about 15 mm. The acceptable tolerances will vary, of course, depending on the product design and customer preferences. It is believed that these variations are the result of inconsistent backsheet stretching, and it is further believed that this inconsistent stretching can be reduced using conventional methods to provide even greater accuracy.

As described above, an absorbent article produced according to the present invention does not have a reference marker corresponding with the graphic 21 on the final absorbent article 10. Unlike U.S. Pat. No. 5,286,543 and other similar prior art with complex feedback control mechanisms, it has been discovered that the graphic(s) 21 can still be properly placed on the final product in an automated manufacturing line without the necessity of including the reference marker(s) 21a on the final product. Furthermore, using the present invention, the graphics 21 can be easily, rapidly and inexpensively attached to the garment by an in-line printing method that does not require the use of pre-printed rolls of graphics.

Although the embodiments of the invention are generally described herein with reference to using a printer to incorporate graphics into absorbent articles, it is also envisioned that the present invention can be used in conjunction with a graphic applicator that places pre-printed graphics onto a substrate or prints without using a rotating cylinder (e.g., bubble jet printers). For example, printer 85 can be replaced with a cut-and-space (also called cut-and-place) device that cuts a graphic from a continuous web of graphics, spaces the individual graphics from one another using a vacuum slip drum, and applies them to a substrate one at a time.

Figure 5:
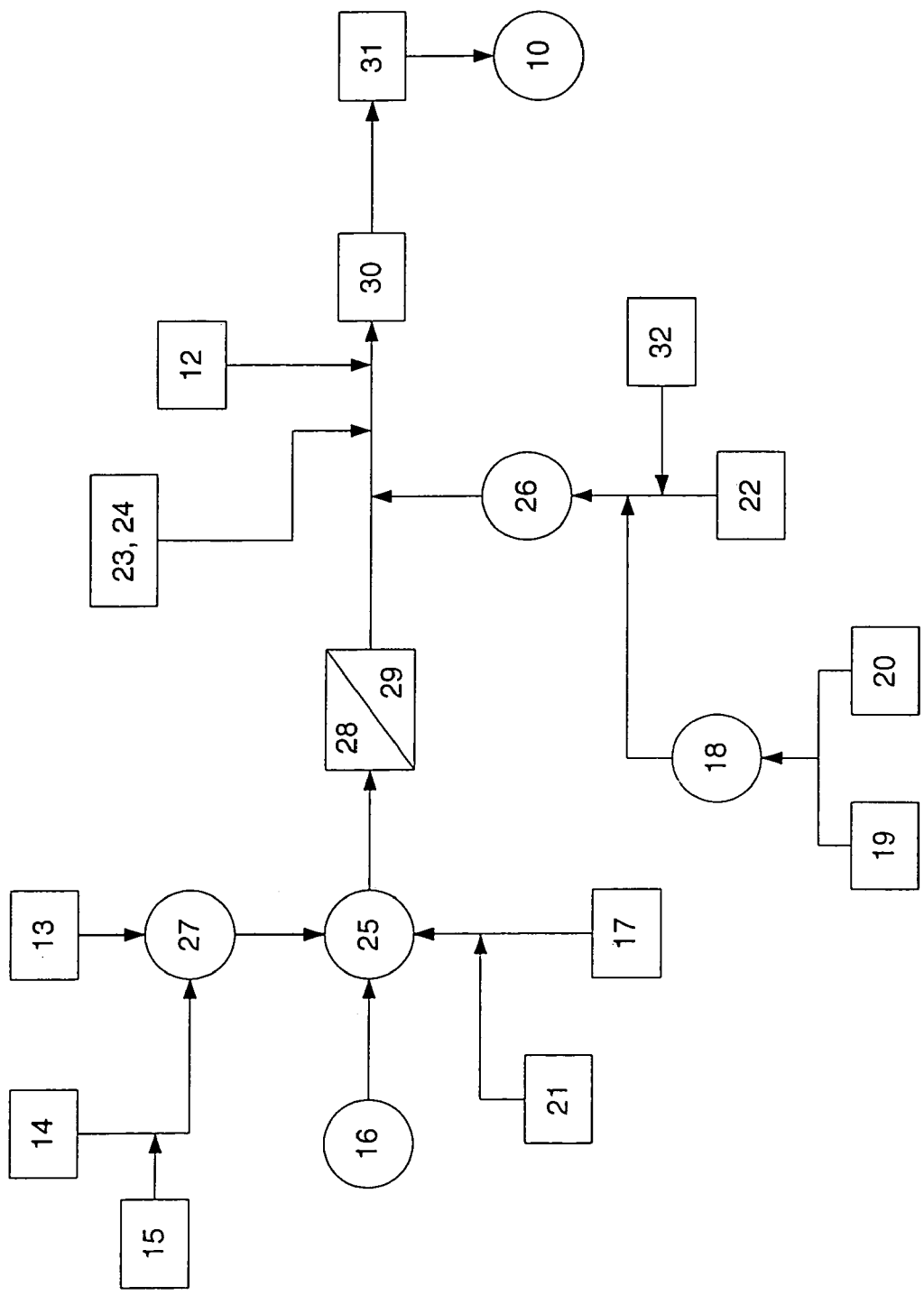
FIG. 5 is a schematic of a preferred method for making an absorbent article according to the present invention.

The absorbent articles of the present invention can preferably be produced according to the system schematically illustrated in the flow diagram of FIG. 5. Generally stated, the method includes the steps of forming a continuous absorbent core assembly 25 that includes printed graphics 21 in the general machine direction (MD); cutting the continuous core assembly into discrete absorbent cores 28; turning the discrete absorbent cores 28 by 90 degrees so that they are pointed in the cross machine direction (CD) but still traveling in the machine direction; attaching the discrete absorbent cores 28 to the non-woven layer 22; and cutting the joined assembly to form discrete absorbent articles 10. In one embodiment, the non-woven layer 22 is provided with graphics (not shown) before being joined with the discrete absorbent cores 28. In this embodiment, the non-woven layer 22 may be referred to as an appliqué layer 26.

The absorbent core assembly 25 can include a central absorbent pad 16 comprising a pulp/SAP absorbent pad wrapped in tissue 16' (FIG. 6A). The absorbent pad 16 can be continuously formed in a manufacturing line by any method known in the art, such as through the deposition of fluff and SAP on a drum-type air forming apparatus.

The absorbent core assembly 25 can further include a topsheet assembly layer 27 and a liquid impermeable backsheet layer 17. The absorbent core assembly 25 can be continuously produced by providing a MD continuously moving absorbent pad 16, a MD continuously moving topsheet assembly layer 27, and a MD continuously moving liquid impermeable backsheet layer 17; layering the absorbent pad 16 between the topsheet layer 27 and the backsheet layer 17; and securing the layers together to form the absorbent core assembly 25. As such, the components are provided, layered, and secured in the general machine direction. In one embodiment, the absorbent pad 16 may be cut into discrete core pieces and spaced apart before being attached to the backsheet 17 and topsheet 14 so that the core pieces only extend along a portion of the length of the topsheet 14 and backsheet 17 in the final assembled article 10.

The topsheet assembly layer 27 can include a non-woven topsheet layer 14, a transfer layer 15, and leg gathers 13. The topsheet assembly layer 27 can be continuously produced by providing a MD continuously moving transfer layer 17 (which may be cut and spaced before attachment, as described above with reference to the absorbent pad 16), a MD continuously moving non-woven topsheet layer 14, and a pair of MD continuously moving leg gathers 13; layering the topsheet layer 14 on top of the transfer layer 15; securing the layers together; and attaching the leg gathers 13 to the side edges of the topsheet layer 14 on the side opposite the transfer layer 15 to form the topsheet assembly layer 27. Again, the components are provided, layered, and secured in the general machine direction.

The MD continuously moving discrete absorbent cores 28 are then individually turned at step 29 to be oriented in the cross machine direction. The turned, continuously moving discrete absorbent cores 28 are joined with an appliqué layer 26, and sealed at step 30. The appliqué layer 26 preferably comprises a non-woven outer layer 22 to which graphics (not shown) are applied, and to which is joined a set of elastic side panels 18. A preferred method for attaching graphics to the non-woven layer 22 is provided in U.S. Pat. No. 6,558,499 to Pargass et al., which is incorporated herein by reference. Alternatively, the present invention may be modified to print the optional graphics onto the non-woven layer 22. The elastic side panels 18 each comprise a pair of carrier strips 19 that encase and are elasticized by elastic elements 20, as previously described. Elastic waist elements 23, elastic leg elements (not shown), and non-woven end strips 12 can also be applied at predetermined locations before or after the appliqué layer 26 has been joined with the discrete absorbent cores 28. The combined core/appliqué structure is folded, bonded and cut at predetermined locations at step 31 to form discrete absorbent articles 10.

Figure 6B:
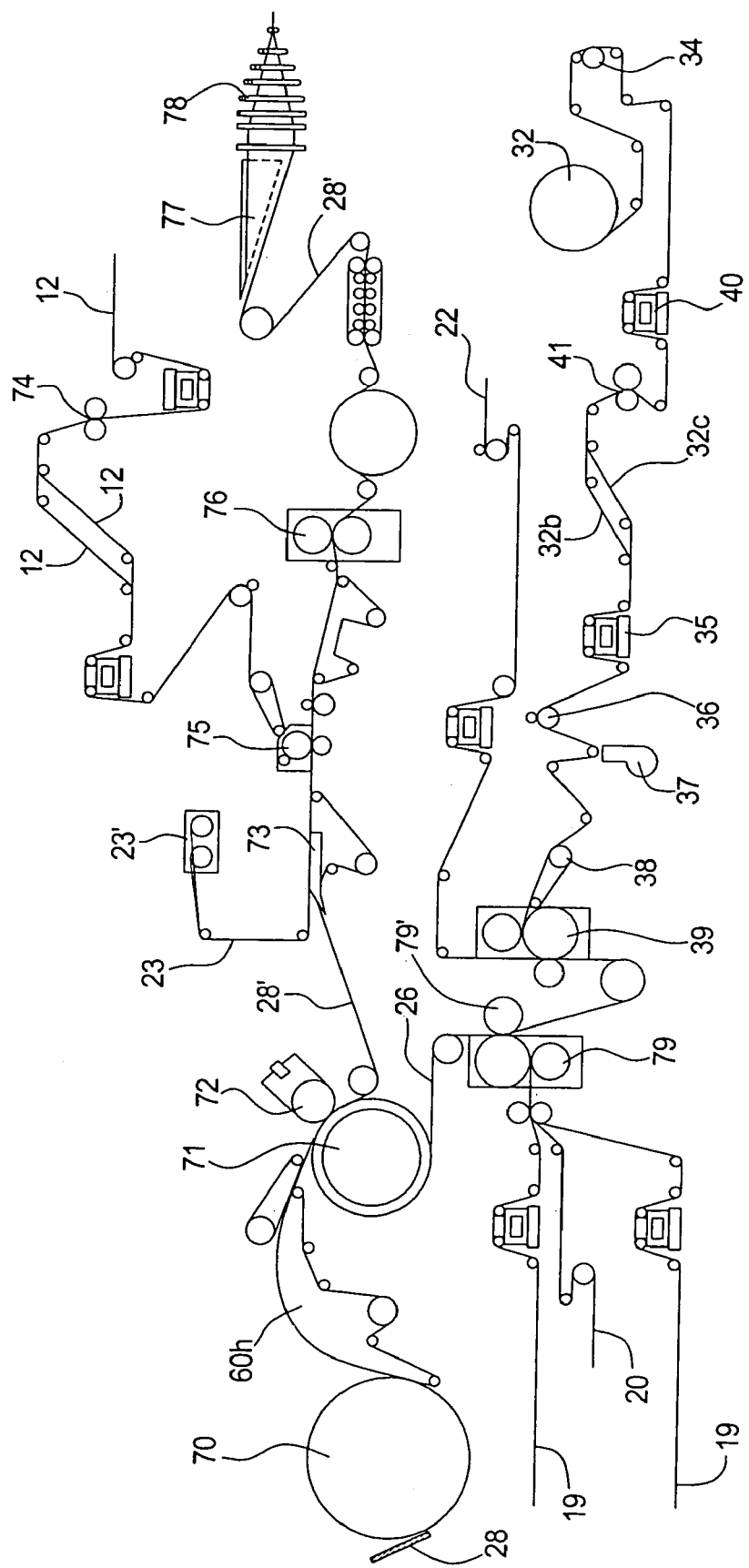
Figure 6C:
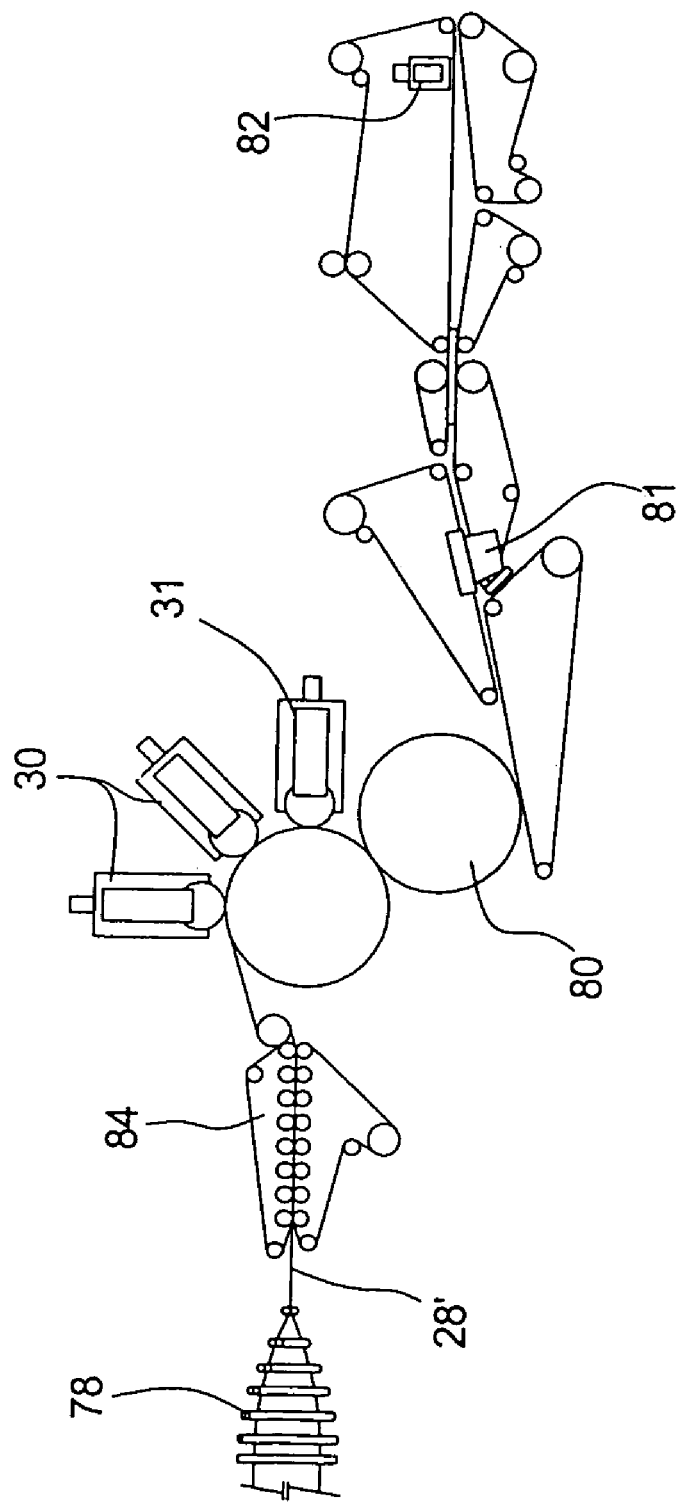

In a particularly preferred embodiment of the present invention, the absorbent articles can be produced in an automated manufacturing line as depicted in FIGS. 6A–6C. Specific mechanisms are provided along, and as part of, the manufacturing line for engaging, conveying, acting against, or otherwise operating on, or relative to, at least one component of the absorbent article being formed.

The mechanisms in the manufacturing line for operating on, or relative to, a component of the absorbent article may include special or conventional mechanisms. The details of such mechanisms, and the detailed method of operation of such mechanisms, will be apparent to those having skill in the art and the detailed descriptions of such mechanisms are not necessary to an understanding of the invention. However, a brief description of the location and purpose of some of the mechanisms is presented to serve as examples of the types of mechanisms with which the present invention may be employed as described in detail hereinafter.

Referring first to the left-hand end of FIG. 6A, a central absorbent pad 16 is introduced into the manufacturing line. The central absorbent pad 16 can be a continuous web supplied from a suitable bulk roll supply (not illustrated). In other modes of operations, a pocket former or drum former (not illustrated) may be provided upstream of the manufacturing line to form individual, and optionally contoured, central absorbent pads 16 of blown, non-woven fluff material. Optionally, the pads 16 may be impregnated with superabsorbent polymer to increase the absorbent capacity of the pads 16. The pads can then be conveyed seriatim in a spaced array through the manufacturing line.

The individual central absorbent pads or the continuous, central absorbent pad 16 are conveyed down the manufacturing line (toward the right as viewed in FIG. 6A) by conveyor 60*a*. A vacuum hold-down system (not illustrated) may be provided along the conveyor 60*a*, and along other conveyors in the manufacturing line, to maintain the components flat and to center the components so as to provide for proper placement of the various components during the manufacturing operations. The mechanical and structural details per se of the conveyor, of the vacuum system, and of other similar conveyors and vacuum systems in the manufacturing line are generally known in the art.

As mentioned previously, central absorbent pad 16 can be wrapped with a tissue layer 16'. As illustrated in FIG. 6A, the tissue wrap 16' can be provided from a supply roll (not shown), wrapped around the central absorbent pad 16, and the wrapped absorbent pad can then be fed through a debulker 61 to compress the tissue and absorbent pad. The supply roll, debulker, motor-driven unwind mechanisms, and other associated mechanisms operate in a conventional manner.

The compressed absorbent pad 16 is moved forward from the debulker 61 by a draw conveyor 60*b* to a pad knife mechanism 62 that severs the central absorbent pad 16 at intervals to provide separate absorbent pads. The separate absorbent pads are conveyed downstream of the knife mechanism 62 by a spacing conveyor 60*c*, which has a linear speed greater than the linear speed of the draw conveyor 60*b* so as to separate the individual absorbent pads and provide a desired end-to-end spacing.

The spacing conveyor 60*c* feeds the spaced-apart absorbent pads to a sealer 63 where the liquid impermeable backsheet layer 17 and the topsheet assembly layer 27 are combined with the absorbent pads 16. The backsheet layer 17 and topsheet assembly 27 are fabricated and partially assembled in other mechanisms in the machine as will next be explained.

As stated previously, the topsheet assembly layer 27 is formed from a non-woven topsheet layer 14, a transfer layer 15, and leg gathers 13. The topsheet 14 is provided from a supply roll (not shown), fed by conveyor 60*d*, and joined with transfer layer 15 at drum 64. Transfer layer 15 is provided from a supply roll (not shown), fed by conveyor 60*e* through cutter 65, and joined with topsheet 14 at drum 64. The joined transfer layer 15 and topsheet 14 are then fed by conveyor 60*f* to sealer 66 where the leg gathers 13, the topsheet 14, and the transfer layer 15 are all joined together to form the topsheet assembly 27.

It will be readily understood that the topsheet layer 14, transfer layer 15 and other layers can be supplied from conventional feed rolls that are aligned parallel with or at an angle with the rest of the machinery. When provided at an angle, turning bars 83 may be used to reorient the layers to the desired orientation. It will also be apparent to those of ordinary skill in the art that various adhesive applicators and other devices necessary to attach the various parts to one another have been omitted from FIGS. 6A–6C in the interest of maintaining the clarity of the drawings. Such devices are well known in the art and a detailed discussion of them is not required herein for understanding the present invention.

The leg gathers 13 are formed from leg gather sheet 13*a* and leg gather elastics 13*b*. The leg gather sheet 13*a* is fed through slitter 67 to form two discrete leg gather sheets. Leg gather elastics 13*b* are fed forward and joined with the two discrete leg gather sheets. The joined elastics and leg gather sheets are then fed through folder 68 to form leg gathers 13. The leg gathers 13 are then fed through sealer 66 where the topsheet assembly 27 is formed. The leg gather elastics 13*b* are secured to the leg gather sheets by a conventional device that (1) provides a continuous length of elastic 13*b* along the sheets 13*a*, (2) separates the elastic into a plurality of continuous, substantially parallel filaments, and (3) tensions the elastic filaments as the elastic filaments are fed against the leg gather sheets 13*b*.

The liquid impermeable backsheet layer 17 is initially supplied in the form of a continuous backsheet web from a backsheet web supply roll (not shown). The backsheet supply roll and associated operating mechanisms operate in a conventional manner. The backsheet is printed with graphics 21 at printer 85, as previously described in detail herein with reference to FIGS. 3 and 4.

The printed backsheet layer 17, topsheet assembly 27, and absorbent pads 16 are fed forward to sealer 63 where the backsheet layer 17 is then attached to (1) the separate absorbent pads and (2) the portions of the top sheet assembly layer 27 which extend beyond the separate absorbent pads. The completed topsheet assembly 27 is drawn through sealer 63 and attached with the absorbent pads 16 and underlying backsheet layer 17. All of the component pieces of the absorbent core assembly 25 are assembled in the proper relationship at sealer 63, as explained elsewhere herein. Once the absorbent core assembly 25 is formed, the MD continuously moving absorbent core assembly 25 is fed through cutter 69 and cut at predetermined locations to form MD continuously moving discrete absorbent cores 28 having graphics 21 printed thereon in the desired location.

With reference to FIG. 6B, the MD continuously moving discrete absorbent cores 28 are then transferred onto turn drum 70 and rotated approximately 90° to travel in the general cross direction (CD). Once turned, the CD continuously moving discrete absorbent cores 28 are transferred onto assembly drum 71, where they are joined together with appliqué layer 26 and sealed by end side sealer 72 to form sealed assemblies 28'. The turn drum 70 also may have radially-variable arms that not only turn the cores 28, but also radially extend or contract to increase or decrease the linear velocity of the cores 28 (with larger radii resulting in greater velocities, assuming the turn drum 70 rotates at an approximately constant speed). Using such an apparatus, the absorbent cores 28 may be picked up at a supply conveyor 60*g* moving at a first speed, and deposited at a receiving conveyor 60*h* having a different speed.

It should be noted that when the appliqué layer 26 is joined together with the CD continuously moving discrete absorbent cores 28 and sealed to form the sealed assemblies 28', the appliqué layer 26 and the non-woven carrier strips 19 (FIG. 2) (described in more detail below) which contain the discrete elastic side panels 18 are continuous and thereby interconnect the individual discrete absorbent core assemblies 28 in the sealed assemblies 28'.

With reference to the right side of FIG. 6B, the fabrication of appliqué layer 26 is illustrated. First, a continuously moving master roll 32, including a series of aesthetically corresponding graphics (not shown), is fed through web guide 40 by conveyor 34. These optional graphics may or may not be related, in location, appearance, subject matter, or in any other way, to the graphics 21 printed on the backsheet 17. Once centered by web guide 40, master roll 32 is fed through slitter 41, where it is separated into two separate master rolls 32*b* and 32*c*. It will be appreciated that web guides 40 can be used throughout the machinery to maintain the supplies of material in the proper location.

Each separate master roll 32*b*, 32*c* can then be identically processed according to the method described herein. However, for ease of reference, only the processing of separate master roll 32*b* will be described with the understanding that master roll 32*c* is processed similarly.

Master roll 32*b* is conveyed past photo-eye/web guide 35, where the location of reference markers on the master roll 32*b* are sensed. Once the reference markers have been sensed, master roll 32*b* is fed through slitter 36, where the reference markers are separated from master roll 32*b* and removed by vacuum pump 37. Master roll 32*b* is then conveyed by servodrive 38 through appliqué cutter 39, where master roll 32*b* is cut into individual segments at predetermined locations based on the location of the previously identified but now removed reference markers. Individual segments of graphics are then applied to non-woven outer layer 22 at appliqué cutter 39 to form a graphic-containing appliqué layer 26. Because photo-eye 35 and appliqué cutter 39 are near one another, the reference markers may be removed from the master roll web 32*b* prior to placement of the individual graphic segments onto the non-woven outer layer 22. As previously noted, the placement of the optional graphics is preferably accomplished using the method described in U.S. Pat. No. 6,558,499 to Pargass et al., but other methods may be used.

The non-woven outer layer 22 is provided from a continuous supply roll (not shown). The non-woven outer layer 22 supply roll and associating operating mechanisms operate in a conventional manner. Once the optional graphics are applied, the graphic containing non-woven layer is then conveyed forward and joined with discrete elastic side panels 18 by a press roll 79' at elastics cutter 79.

With reference to the left side of FIG. 6B, discrete elastic side panels 18 are formed from carrier strips 19 and side panel elastic elements 20 (see also FIG. 2). The carrier strips 19 and side panel elastic elements 20 are provided from continuous supply rolls (not shown). The carrier strips 19 are conveyed forward and joined with side panel elastic elements 20 using an intermittent adhesive pattern so that only portions of the elastic elements 20 are glued to the carrier strips 19, while the remaining portions remain unglued. The joined elastic/carrier strip assembly is then fed through elastics cutter 79, where the side panel elastic elements 20 are cut along a longitudinal centerline (where the elastics 20 are unglued) to form discrete elastic side panels 18. It is noted that the elastic elements 20 are cut along a longitudinal centerline where they are unglued such that they "snap back" to provide elasticity to the side portions of the assembly, while leaving the center portion unelasticized (see FIGS. 1 and 2). The carrier layers 19, which include the elastic side panels 18, are then joined with the graphic-containing non-woven layer to form appliqué layer 26. The appliqué layer 26 is then conveyed forward and joined together with the CD continuously moving discrete absorbent cores 28 to form the sealed assemblies 28', as described above. The machinery is coordinated such that the discrete absorbent cores 28 are placed between the discrete elastic side panels 18 (i.e., on the unelasticized center portion) so that they are located in the articles 10 as shown in FIG. 2.

Once appliqué layer 26 is joined with the CD continuously moving discrete absorbent cores 28 and sealed by sealer 72 to form sealed assemblies 28', waist elastic elements 23 are applied to the peripheral edges of the sealed assemblies 28'. The waist elastic elements 23 are provided from a continuous supply of elastic strands 23' and placed on the sealed assemblies 28' using conventional placement techniques. The waist edges of the sealed assemblies 28' are then folded over the waist elastic elements 23 by waist folder 73. Leg elastics (not shown) also may be applied to the assembly to ultimately be positioned along the leg openings 24 of the article 10, as known in the art.

Non-woven end strips 12 are then applied to the sealed assemblies 28'. The non-woven end strips 12 are supplied from a continuous roll of non-woven web (non shown). The supply web is cut into separate left and right side end strips 12 at slitter 74. The individual end strips 12 are then cut by cutter 75 at a predetermined location, conveyed forward and joined with sealed assemblies 28'. Alternatively, the non-woven end strips 12 may be supplied and attached as a continuous supply that, in the final product, extends across the entire width of the article 10.

Once the non-woven end strips 12 are applied to the CD continuously moving discrete sealed assemblies 28', the sealed assemblies 28' are conveyed forward and fed through leg hole cutter 76, where the side edges of the sealed assemblies 28' are trimmed to provide appropriate leg hole openings 24 (FIG. 2). The CD continuously moving discrete sealed assemblies 28' are then folded along the lateral centerline of the individual assemblies by bi-folder 77 to orient the CD continuously moving discrete sealed assemblies 28' such that the front waist portions 10a and rear waist portions 10b oppose each other.

The folded assemblies 28' are then rotated 90° at twist-conveyor 78 and, with reference to FIG. 6C, conveyed to heat seal unit 30 where the side edges of the folded assemblies 28' are sealed to complete the formation of the elastic side panels 18 (as shown in FIG. 1). A press roll assembly 84 may be used to compress the folded assembly 28' in preparation for the heat sealing process. Once the side edges are sealed, the assemblies are passed through final cutter 31 to form individual absorbent articles 10. The sealed assemblies 28' are separated into individual absorbent articles 10 at final cutter 31 by severing the appliqué layer 26 and continuous non-woven carrier strips 19 interconnecting the discrete absorbent cores 28 at predetermined locations between each of the discrete absorbent cores 28. The placement and cutting of the sealed assemblies 28' are accomplished using conventional registration and placement methods.

The individual absorbent articles 10 are then transferred to turning drum 80, which turns them 90 degrees, and conveyed to rejector 81 where the individual absorbent articles 10 are rejected if they fail any of a number of quality monitoring stations (not shown) that may be located throughout the assembly line. The final absorbent articles 10 conforming with quality checks are then conveyed to tack hold 82 for packaging.

In one preferred embodiment, the various machinery components are driven by a unitary drive system that uses a single drive shaft to rotate many or all of the components. In this embodiment, the components are attached to the main drive shaft by pulleys, gears or the like that drive the components at a linearly proportional speed relative to the main drive shaft. Such a unitary drive system is disclosed, for example, in U.S. Pat. No. 5,383,988 to Herrmann et al., which is incorporated herein by reference. In another preferred embodiment, however, the unitary drive may be omitted in whole or in part, and the various machinery components may be driven by individual or linked motors or servodrives that maintain the machinery components at essentially linearly proportional speeds relative to one another. Of course, in any embodiment, some components may operate at variable speeds (i.e., accelerating or decelerating while the PPM remains constant) or may operate at speeds that do not have a linearly proportional relationship to the overall PPM. In any of these embodiments, the speed of any of the components may be used to generate the line speed reference signal to calculate the PPM, provided that the component's operating speed is capable of being measured and there is a discernable mathematical relationship between the component's operating speed and the overall PPM. The calculation of PPM and the mathematical relationship between the line speed target component's speed and the printer speed will be readily understood by those of ordinary skill in the art.

The invention has been described in connection with the above preferred embodiments. These embodiments, however, are merely illustrative and the invention is not restricted thereto. It will be understood by those skilled in the art that other variations and modifications can easily be made within the scope of the invention as defined by the appended claims.

I claim:

1. A system for incorporating graphics into absorbent articles, the system comprising:
   a substrate web path adapted to provide a moving substrate to a print cylinder
   a line speed reference signal sensor associated with a line speed target machinery component comprising the main drive and adapted to generate a line speed reference signal, said line speed reference signal sensor comprising an encoder that measures the angular velocity of the main drive;
   a phase difference signal sensor associated with a phase target machinery component and adapted to generate a phase difference signal; and
   a printer controller adapted to operate the print cylinder at a predetermined speed based on the line speed reference signal, to thereby print a series of graphics on the moving substrate at predetermined distance frequency;
   the printer controller being further adapted to set an actual print cylinder phase angle, based on the phase difference signal, to approximate a predetermined phase angle to thereby position the series of graphics on the moving substrate at a series of desired graphics locations.

2. The system of claim 1, wherein the moving substrate comprises a backsheet web.

3. The system of claim 2, wherein the system further comprises:
   an absorbent pad supply path adapted to convey an absorbent pad supply;
   a topsheet web path adapted to provide a topsheet web;
   a sealer adapted to join the topsheet web to the backsheet web with the absorbent pads located therebetween to thereby form an absorbent core assembly; and
   a cutter adapted to cut the absorbent core assembly at a series of cuts;
   wherein the phase target machinery component comprises the cutter.

4. The system of claim 1, wherein the phase target machinery component comprises a cutter.

5. The system of claim 1, wherein the line speed target machinery component and the phase target machinery component comprise different machinery components.

6. The system of claim 1, wherein the line speed target machinery component and the phase target machinery component comprise the same machinery component.

7. The system of claim 1, wherein the phase difference signal sensor comprises an inductance sensor.

8. The system of claim 1, wherein the series of graphics comprises a series of wetness indicators.

9. The system of claim 1, wherein the series of graphics comprises a series of combined wetness indicators and decorative graphics.

10. The system of claim 1, wherein the print cylinder comprises a flexographic print cylinder.

11. The system of claim 1, wherein the system further comprises:
a second print cylinder, wherein the substrate web path is adapted to provide the moving substrate to the second print cylinder; and
wherein the printer controller is further adapted to rotate the second print cylinder at the predetermined speed, to thereby print a second series of graphics on the moving substrate at the predetermined distance frequency.

12. The system of claim 11, wherein the series of graphics comprises a series of wetness indicators and the second series of graphics comprises a series of decorative graphics.

13. The system of claim 1, wherein the printer controller is further adapted to detect a shutdown mode from the line speed reference signal, disengage the print cylinder from the substrate, and rotate the print cylinder at an idle speed.

14. The system of claim 1, wherein the printer controller is further adapted to detect a startup mode from the line speed reference signal, accelerate the print cylinder from an idle speed to the predetermined speed, and engage the print cylinder with the moving substrate.

15. The system of claim 1, wherein the substrate with the series of graphics printed thereon is incorporated into an absorbent article, the absorbent article being selected from the group consisting of a baby diaper, a baby training pant, and an adult incontinence article.

16. A system for incorporating graphics into absorbent articles, the system comprising:
a substrate web path adapted to provide a moving substrate to a graphic applicator;
a line speed reference signal sensor associated with a line speed target machinery component comprising the main drive and adapted to generate a line speed reference signal, said line speed reference signal sensor comprising an encoder that measures the angular velocity of the main drive;
a phase difference signal sensor associated with a phase target machinery component and adapted to generate a phase difference signal; and
a graphic applicator controller adapted to operate the graphic applicator at a predetermined speed, based on the line speed reference signal, to thereby apply a series of graphics on the moving substrate at a predetermined distance frequency;
the graphic applicator controller being further adapted to set an actual graphic applicator phase angle, based on the phase difference signal, to approximate a predetermined phase angle to thereby position the series of graphics on the moving substrate at a series of desired graphics locations.

17. The system of claim 16, wherein the moving substrate comprises a backsheet web.

18. The system of claim 17, wherein the system further comprises:
an absorbent pad supply path adapted to convey an absorbent pad supply;
a topsheet web path adapted to provide a topsheet web;
a sealer adapted to join the topsheet web to the backsheet web with the absorbent pads located therebetween to thereby form an absorbent core assembly; and
a cutter adapted to cut the absorbent core assembly at a series of cuts;
wherein the phase target machinery component comprises the cutter.

19. The system of claim 16, wherein the phase target machinery component comprises a cutter.

20. The system of claim 16, wherein the line speed target machinery component and the phase target machinery component comprise different machinery components.

21. The system of claim 16, wherein the line speed target machinery component and the phase target machinery component comprise the same machinery component.

22. The system of claim 16, wherein the phase difference signal sensor comprises an inductance sensor.

23. The system of claim 16, wherein the series of graphics comprises a series of wetness indicators.

24. The system of claim 16, wherein the series of graphics comprises a series of combined wetness indicators and decorative graphics.

25. The system of claim 16, wherein the graphic applicator is a cut-and-space device.

26. The system of claim 16, wherein the graphic applicator controller is further adapted to detect a shutdown mode from the line speed reference signal, and disengage the graphic applicator from the substrate.

27. The system of claim 16, wherein the graphic applicator controller is further adapted to detect a startup mode from the line speed reference signal, accelerate the graphic applicator to the predetermined speed, and engage the graphic applicator with the moving substrate.

28. The system of claim 16, wherein the substrate with the series of graphics applied thereto is incorporated into an absorbent article, the absorbent article being selected from the group consisting of a baby diaper, a baby training pant, and an adult incontinence article.

* * * * *